United States Patent [19]

Blum et al.

[11] Patent Number: 5,008,422

[45] Date of Patent: * Apr. 16, 1991

[54] POLYSILAZANES AND RELATED COMPOSITIONS, PROCESSES AND USES

[75] Inventors: Yigal D. Blum, Menlo Park; Richard M. Laine, Palo Alto, both of Calif.

[73] Assignee: SRI International, Menlo Park, Calif.

[ * ] Notice: The portion of the term of this patent subsequent to Sep. 16, 2003 has been disclaimed.

[21] Appl. No.: 12,874

[22] PCT Filed: Oct. 24, 1986

[86] PCT No.: PCT/US86/02266

§ 371 Date: Dec. 1, 1986

§ 102(e) Date: Dec. 1, 1986

Related U.S. Application Data

[63] Continuation-in-part of Ser. No. 908,685, Mar. 4, 1986, which is a continuation-in-part of Ser. No. 727,415, Apr. 26, 1985, Pat. No. 4,612,383.

[51] Int. Cl.$^5$ .................................................. C07F 7/10
[52] U.S. Cl. .................................. 556/412; 586/402; 586/410
[58] Field of Search ........................ 556/410, 412, 402

[56] References Cited

U.S. PATENT DOCUMENTS

| | | | |
|---|---|---|---|
| 4,482,689 | 11/1984 | Haluska | 528/25 |
| 4,540,803 | 9/1985 | Cannady | 556/412 |
| 4,656,300 | 4/1987 | Lebrun et al. | 556/412 |
| 4,666,872 | 5/1987 | Baney et al. | 501/88 |
| 4,668,642 | 5/1987 | Bujalski | 501/88 |
| 4,675,424 | 6/1987 | King, III et al. | 556/412 |
| 4,689,382 | 8/1987 | Lebrun et al. | 528/12 |

*Primary Examiner*—Paul F. Shaver
*Attorney, Agent, or Firm*—Irell & Manella

[57] ABSTRACT

Silazanes and related compounds are prepared by (a) providing a precursor containing at least one Si-N bond, cleaving an Si-N bond in the precursor in the presence of hydrogen or a hydrogen donor, and reacting the cleavage product with a second cleavage product or with a compound containing an Si-H bond, an N-H bond, or both, to produce an initial silazane product having at least one newly formed Si-N bond or (b) providing one or more reactants which contain an Si-H bond and an N-H bond, and causing reaction to occur between the two bonds in the presence of a transition metal catalyst to form an initial silazane product having newly formed Si-N bonds. Further products may result from additional reaction of either type. Novel compounds, including siloxazanes and high molecular weight polysilazanes, are provided. The compounds may be pyrolyzed to yield ceramic materials such as silicon nitride, silicon carbide and silicon oxynitride. In a preferred embodiment, substantially pure silicon nitride and articles prepared therefrom are provided. Fibers coatings, binders, and the like may be prepared from the novel materials.

11 Claims, 4 Drawing Sheets

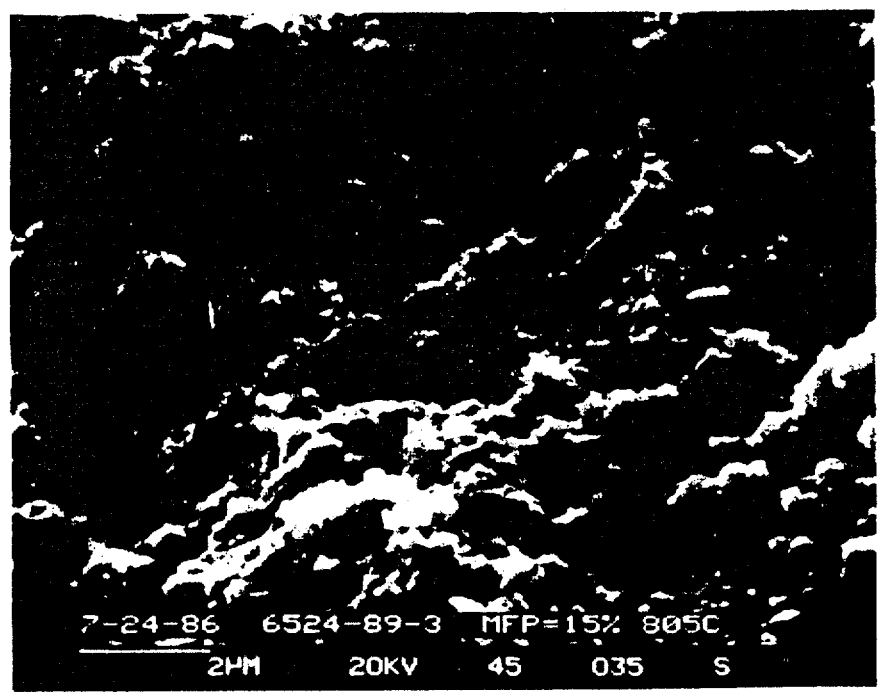
FIG. 3 SEM PHOTOGRAPH OF FORMED $Si_3N_4$/POLYSILAZANE BODY AFTER HEATING TO 800°C IN $N_2$
This body contained 15 wt% polymer.

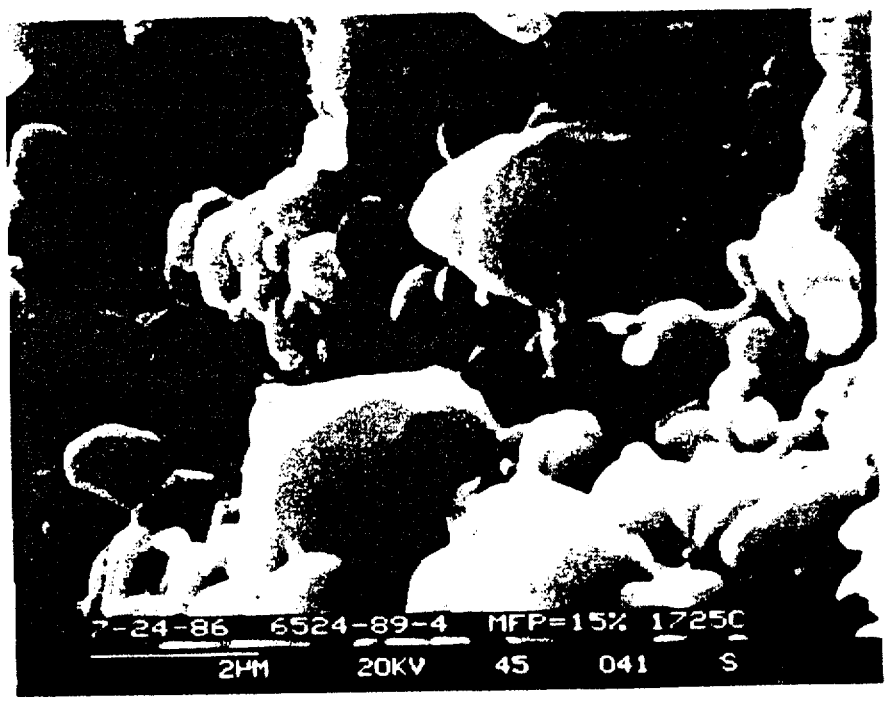
FIG. 4 SEM PHOTOGRAPH OF FORMED $Si_3N_4$/POLYSILAZANE BODY AFTER HEATING TO 1725°C IN $N_2$
Note considerable grain growth and enlargement of pores relative to previous figure.

POLYSILAZANES AND RELATED COMPOSITIONS, PROCESSES AND USES

ORIGIN OF INVENTION

The Government has certain rights in this invention as it was funded in Part under Contract Nos. N00014-84-C-0392 and N00014-85-C-0668 awarded by the Office of Naval Research.

CROSS-REFERENCE TO RELATED APPLICATIONS

This application is a continuation-in-part of U.S. application Ser. No. 908,685, filed Mar. 4, 1986 (PCT/US86/00548), which is a continuation-in-part of U.S. application Ser. No. 727,415, filed Apr. 26, 1985, now issued as U.S. Pat. No. 4,612,383.

DESCRIPTION

1. Technical Field

The invention relates to the synthesis of compounds (by which it is intended to include monomers, oligomers and polymers) containing the structure Si—N in the molecule. The invention concerns primarily lazanes and their derivatives, which may be pyrolyzed to yield a variety of ceramic products, and also relates to siloxazanes (by which it is meant monomers, oligomers and polymers containing the O—Si—N unit) and other compounds containing one or more Si—N bonds. The invention additionally relates to the synthesis of novel, high molecular weight polysilazanes and their precursors, and the use of these unique compounds for the fabrication of ceramic coatings, fibers, binders, and injection-molded articles. The invention also relates to the use of polysiloxazanes and polyhydridosiloxanes as ceramic precursors.

2. Background

Polysilazanes and their derivatives are useful among other things, for the preparation of silicon nitride ($Si_3N_4$, silicon carbide (SiC), $Si_3N_4$/SiC alloys, $Si_3N_4$/carbon alloys, $Si_3N_4$/boron nitride alloys, and mixtures thereof. These ceramic materials can be used as structural materials, protective coatings, and electronic materials because of their hardness, strength, structural stability under extreme environmental conditions and their wide variety of electronic properties. In particular, these materials can be formed into ceramic fibers of value for reinforcement of composite materials. See, for example, (a) Department of Defense Proceedings, Fourth Metal Matrix Composites Technical Conference, May 19–21, 1981, prepared for DOD Metal Matrix Composites Information Analysis Center; and (b) J. J. Brennan, "Program to Study SiC Fiber-Reinforced Matrix Composites", Annual Report to Dept. of Navy (Nov. 1980), Contract No. N00014-78-C-0503.

Historically, polysilazanes were first synthesized by Stock et al almost 60 years ago (see, e.g., Stock, A. and K. Somieski, Ber. Dtsch. Chem. Ges. 54:740 (1921)) via a simple ammonolysis technique (Scheme I). However, this

  

Scheme I approach usually produces mixtures of cyclomers where x is 3 to 5 that are obtained as the major products and small amounts of linear oligomers where y is less than or equal to about 10. Because of their low molecular weight, however, these linear oligosilazanes are too volatile to be used as preceramic materials.

In order to obtain higher molecular weight, nonvolatile materials, it was necessary to promote cross-linking reactions. In this manner, moderate molecular weight polysilazanes have been synthesized using a variety of techniques. See, e.g., Kruger, C. R. and E. G. Rochow, J. Polymer Sci. 2A:3179–3189 (1964). Rochow et al. discovered that ammonium chloride catalyzes cross-linking in simple oligodimethylsilazanes to form polysilazanes (Scheme II) which

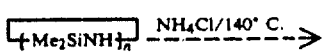 

Scheme II $\overline{M}_n = 10{,}000$ D were proposed to contain cyclic monomer units cross-linked through nitrogen as suggested by the structure of Formula 1.

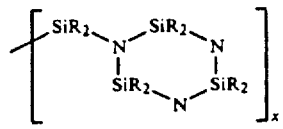

Formula 1

The Penn et al. work follows up on U.S. Pat. Nos. 3,853,567 to Verbeek and 3,892,583 to Winter et al., wherein a high temperature elimination/condensation reaction was shown to lead to soluble, highly cross-linked polymers as shown in Scheme III. Pyrolysis at high temperatures provides ceramic

Scheme III

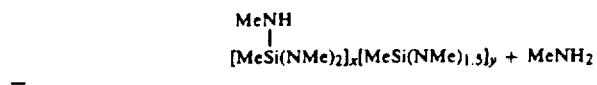

$\overline{M}_w = 4200$ D yields of 60% with a mixture of $Si_3N_4$ and SiC ceramic materials.

A related cross-linking approach described, inter alia, in U.S. Pat. Nos. 4,312,970, 4,340,619, 4,535,007 and 4,543,344 begins with the preparation of tractable polysilazanes having $Me_3Si$ groups linked to the polymer backbone (Scheme IV) with the highest molecular weights reported in the available literature, i.e. about $\overline{M}_w \sim 15{,}000$ D and $\overline{M}_z \sim 39{,}000$ D:

Scheme IV

$\overline{M}_w = 15{,}000$ D $\overline{M}_z = 39{,}000$ D

Ceramic yields obtained from pyrolysis fibers formed from this polymer are on the order of 45–55% with compositions of 96% $Si_3N_4$, 2% carbon and 2% oxygen after curing.

U.S. Pat. No. 4,482,669 to Seyferth et al. discloses that it is possible to cross-link low molecular weight cyclic oligomers containing Si—H bonds adjacent to N—H bonds via the following reaction:

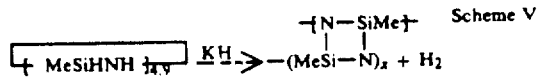

The NH bond is catalytically activated by the strong base in this reaction. This type of cross-linking generates two-dimensional polymers, the solubility of which is limited by their sheet-like character. Ceramic yields of these materials are often quite high, up to about 86%, and typically provides $Si_3N_4$, SiC and carbon in a mole ratio of 0.88:1.27:0.75. If the pyrolysis is carried out in an $NH_3$ atmosphere, then the only product is $Si_3N_4$ with the other products remaining as slight impurities.

Zoeckler and Laine in J. Org. Chem. (1983) 48:2539-2541 describe the catalytic activation of the Si—N bond and in particular the ring opening of octamethylcyclotetrasilazane and polymerization of the ring-opened intermediate. Chain termination is effected by introducing [(CH$_3$)$_3$Si]$_2$NH as a coreactant giving rise to polymers (CH$_3$)$_3$Si—[NHSi(CH$_3$)$_2$]$_n$—NH-Si(CH$_3$)$_3$ where n may be 1 to 12 or more depending upon the ratio of the chain terminator to the cyclic silazane. The catalyst used was $Ru_3(CO)_{12}$. Other publications are as follows: W. Fink, Helv. Chem. Acta., 49:1408 (1966); Belgian Patent 665774 (1965); Netherlands Patent 6,507,996 (1965); D. Y. Zhinkis et al., Rus. Chem. Rev., 49:2814 (1980); K. A. Andrianov et al., Dok Akad. Nauk. SSSR, 227:352 (1976); Dok Akad. Nauk. SSSR 223;347 (1975); L. H. Sommer et al., JACS 91:7061 (1969); L. H. Sommer, J. Org. Chem. 32:2470 (1969); L. H. Sommer, J. Org. Chem. 32:2470 (1967); L. H. Sommer et al., JACS 89:5797 (1967).

In general, control of the polysilazane molecular weight, structural composition and viscoelastic properties play a considerable role in determining the tractability (solubility, meltability or malleability) of the polymer, the ceramic yield, and the selectivity for specific ceramic products. In particular, the tractability plays a major role in how useful the polymer is as a binder, or for forming shapes, coatings, spinning fibers and the like. The more cross-linked a polymer is, the less control one has of its viscoelastic properties. Thus, highly cross-linked and low molecular weight polymers are not particularly useful for spinning fibers because the spun preceramic fiber often lacks tensile strength and is therefore unable to support its own weight. By contrast, high molecular weight, substantially linear polymers as provided herein are extremely important. Such polymers represent a significant advance in the art, as they provide chain entanglement interactions in the fiber-spinning process and thus enhance the overall tensile strength of the spun fibers.

An example of how molecular weight correlates with the properties of a particular polysilazane can be illustrated by the properties of ${+H_2SiNMe}_{n}$. The original synthesis of this material was reported by Seyferth et al. in *Ultrastructure Processing of Ceramics, Glasses and Composites*, Ed. Hench et al. (Wiley & Sons, 1984) via an aminolysis reaction:

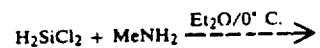

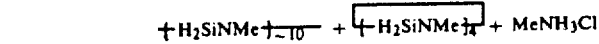

This method of preparation gives a mixture of a volatile cyclotetramer (35%) and nonvolatile oligomers. This mixture has an $\overline{Mn}$ of about 330 D and gives only a 28% ceramic yield upon pyrolysis. Distillation of the volatile cyclomer yields 65% of low molecular weight nonvolatile oligomer ($\overline{Mn}=560$) which is pyrolyzed to give a 39% ceramic yield. An improved method of preparing these oligomers is illustrated by Scheme VII:

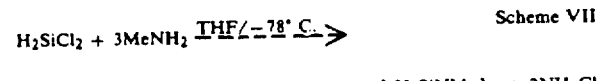

By the method of this invention, working at temperatures of lower than about 0° C. provides mostly nonvolatile linear oligomers (between about 85% and 95%) that require no distillation/purification step. For this product, the $\overline{Mn}$ is about 800–1,100 D (n~14–19). Pyrolysis of this improved oligomer gives significantly higher ceramic yields of 50% with some improvement in product quality, with $Si_3N_4$ purities of above about 80%, the remainder being carbon.

By the method of this invention, the silazane product of Scheme VII can be further polymerized to give novel polymers with $\overline{Mn}$ greater than about 10,000 D, in some cases greater than about 20,000 D, $\overline{Mw}$ greater than about 16,000 D and in some cases greater than about 32,000 D, $\overline{Mz}$ greater than about 40,000 D and in some cases greater than 80,000 D, or with observable species having a molecular weight of higher than about 50,000 and in some cases higher than about 500,000 D. Molecular weights as high as 2,500,000 D (see Example 23) have been detected for the polysilazanes as provided herein. Pyrolysis of these true polymer species will give significantly higher ceramic yields than previously obtained, the ceramic yield to a large extent depending on the molecular weight distribution and the polymer processing. $Si_3N_4$ purities of 80% or higher may be obtained, depending on the reaction conditions.

These novel high molecular weight polymers are soluble, exhibit a high degree of linearity and give higher ceramic yields and $Si_3N_4$ purities than the oligomeric starting material. In addition, the viscoelastic properties of the novel compounds can be carefully controlled using the method of this invention. In particular, at higher molecular weights, these polymers exhibit non-Newtonian viscoelastic properties, allowing for chain entanglement which will increase the tensile strength required to draw the thin precursor fibers required to form ceramic fibers.

The high ceramic yields are of considerable value in binder applications, injection molded parts and in matrix applications. During pyrolysis the density/volume change from preceramic polymer (1–1.3 g/cc) to ceramic (3.2 g/cc for $Si_3N_4$) can be significant. Thus, ceramic yields far below theoretical will only magnify the resulting density/volume change. For example, a 50% ceramic yield for a $Si_3N_4$ precursor of density 1.0 will result in a final decrease in volume of approximately 80%.

It should be noted that certain aspects of the present invention are discussed in co-pending application PCT/US86/00548, U.S. Ser. No. 908,685, filed Mar. 4, 1986, and the parent thereto, U.S. application Ser. No. 727,415, filed Apr. 26, 1985, now issued as U.S. Pat. No. 4,612,383. The disclosures of these related cases are hereby incorporated by reference in their entirety.

DISCLOSURE OF THE INVENTION

It is thus a primary object of the present invention to overcome the aforementioned disadvantages of the prior art.

It is another object of the invention to provide improved methods of preparing silazanes, and, in particular, high molecular weight polysilazanes.

It is still another object to provide methods of preparing siloxazanes and high molecular weight polysiloxazanes.

Still another object of the invention is to provide a method of making silazanes and related compounds using transition metal catalysts which provide an extremely rapid initial reaction rate.

A further object of the invention is to provide novel compounds including siloxazanes and high molecular weight polysilazanes and polysiloxazanes.

Still a further object of the invention is to provide a method of making ceramic materials having a high silicon nitride content, and to prepare and pyrolyze precursors to silicon oxynitride and silicon carbide fine powders.

Another object of the invention is to provide a method of pyrolyzing preceramic materials so as to control the ceramic yield obtained, e.g. by controlling temperature, temperature ramping, pressure, the particular gaseous atmosphere selected, etc.

Still another object of the invention is to provide a method of coating substrates with ceramic materials.

Other objects of the invention include methods of making fibers, fine or monodispersed powders, coatings, porous articles such as ceramic foams, filters and membranes, and compression-molded and injection-molded articles using, inter alia, the preceramic polymers and the ceramic materials as provided herein.

Still other objects of the invention include methods of using the polymers of the invention as binders, as adhesives, in infiltration applications, and in matrix and composite materials.

Additional objects, advantages and novel features of the invention will be set forth in part in the description which follows, and in part will become apparent to those skilled in the art on examination of the following, or may be learned by practice of the invention.

In one aspect of the invention, a monomeric, oligomeric or polymeric precursor containing at least one Si—N bond is provided. An Si—N bond in the precursor is cleaved in the presence of hydrogen or a hydrogen donor, and the cleavage product is reacted with another cleavage product or with a compound containing an Si—H bond, an N—H bond, or both, in the presence of a transition metal catalyst. The initial silazane product so formed has at least one newly formed Si—N bond.

In another aspect of the invention, one or more reactants are provided having an Si—H and an N—H bond, and reaction is caused to occur so as to form hydrogen and a silazane product having at least one newly formed Si—N bond and at least two Si—N bonds in its structure.

Reaction of one type may be caused to follow reaction of the other type; alternatively, both types may be caused to proceed simultaneously, for example, if one or more starting materials are provided having in combination Si—N, Si—H and N—H bonds. Thus, a variety of reaction products can be prepared with these processes.

The silazane products may be provided as preceramic polymers having moderate or very high molecular weight, which polymers in turn provide a correspondingly high ceramic yield upon pyrolysis. As will be discussed below, these high molecular weight polymers may be produced in such a way so as to provide substantially pure silicon nitride upon pyrolysis.

In a preferred embodiment of the invention, the catalysts which are used in the above-described reactions provide rapid reaction rates, on the order of about fifteen to fifty times faster than reactions employing standard catalysts.

The invention also encompasses novel silazane and siloxazane compounds and a variety of applications.

BRIEF DESCRIPTION OF THE DRAWINGS

FIG. 3 is an SEM photograph of a formed $Si_3N_4$/polysilazane body after heating to 800° C. in $N_2$; and FIG. 4 is an SEM photograph of a formed $Si_3N_4$/polysilazane body after heating to 1725° C. in $N_2$.

MODES FOR CARRYING OUT THE INVENTION

Figure 1:
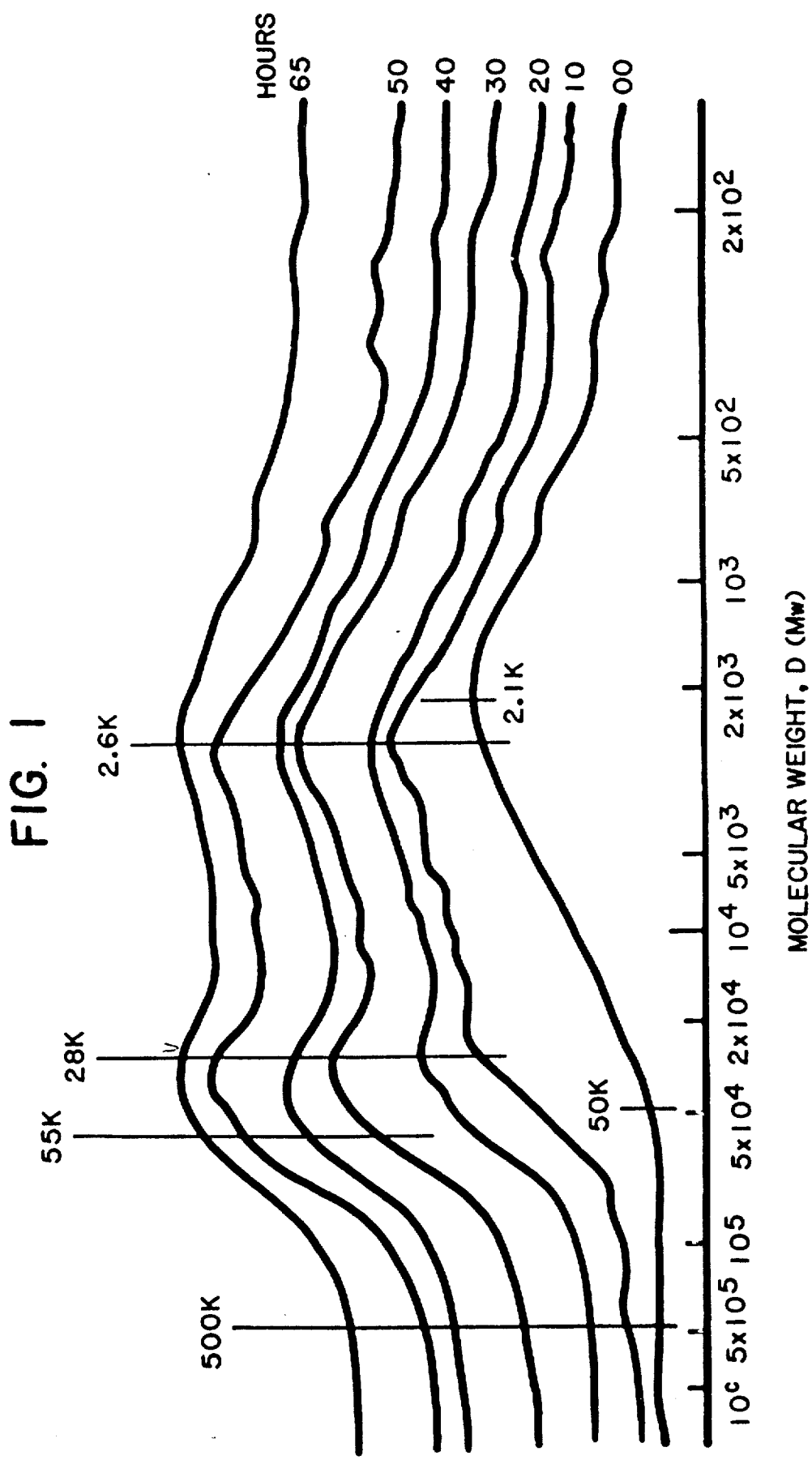
FIG. 1 illustrates the GPC results of a silazane ($[H_2SiNMe]_x$ polymerization catalyzed by $Ru_3(CO)_{12}$.

"Silazanes" as used herein are compounds which contain one or more silicon-nitrogen bonds. The term "polysilazane" is intended to include oligomeric and polymeric silazanes, i.e. compounds which include two or more monomeric silazane units.

"Siloxazanes" as used herein are compounds which contain the unit [O—Si—N]. The term "polysiloxazane" is intended to include oligomeric and polymeric siloxazanes, i.e. compounds which include two or more monomeric siloxazane units.

"High molecular weight" polymers as provided herein are polymers that have an $\overline{Mn}$ greater than about 10,000 D, in some cases greater than about 20,000 D, $\overline{Mw}$ greater than about 16 000 D and in some cases greater than about 32,000 D, $\overline{Mz}$ greater than about 40,000 D and in some cases greater than 80,000 D, or with observable species having a molecular weight higher than about 50,000 D and in some cases greater than 500,000 D.

"$\overline{Mn}$", "$\overline{Mw}$" and "$\overline{Mz}$" are defined as follows. The number average molecular weight $\overline{Mn}$ of a polymer distribution is given by $$\overline{Mn} = \frac{\Sigma Wi}{\Sigma Ni},$$

the weight average molecular weight $\overline{Mw}$ of a polymer distribution is given by $$\overline{Mw} = \frac{\Sigma WiMi}{\Sigma Ni},$$

and the $\overline{Mz}$ value is given by $$\overline{M}_t = \frac{\Sigma WiMi^2}{\Sigma WiMi}$$

wherein Wi is the weight of each individual polymeric or oligomeric species, Ni is the number of individual species in the distribution, and Mi is the mass fraction of each individual species. Where not otherwise specified, molecular weights for a particular polymer distribution obtained directly will be given as calculated prior to any separation or distillation step.

"Substantially linear" oligomers or polymers are non-cyclic structures having two or more monomeric units and which are not extensively cross-linked or branched.

A "substantially pure" ceramic material is intended to mean a ceramic material comprising at least about 75 wt. % of a particular compound.

The "ceramic yield" of a compound upon pyrolysis indicates the ratio of the weight of the ceramic product after pyrolysis to the weight of the compound before pyrolysis.

The "purity" of a particular compound in a mixture of ceramic materials is defined as the weight percent of that compound in the mixture.

"Cyclic silazanes" are cyclic compounds having one or more Si—N bonds in the molecule.

"Silyl," unless otherwise specified, includes siloxyl, siloxazyl and silazyl.

Silazane and siloxazane "copolymers" incorporate more than one type of monomer unit defined as a precursor or reactant in reactions of type (a) or type (b) herein.

A "tractable" polymer is one which is meltable, soluble or malleable or which can be processed like an organic polymer to form a desired shape.

The compounds provided by the processes of the present invention are monomeric, oligomeric or polymeric structures having one or more newly formed Si—N bonds. The reactions which form these structures may be broadly grouped into two types.

In the reaction which will sometimes hereinafter be referred to as the type (a) reaction, a precursor is initially provided which contains at least one Si—N bond. Cleavage of an Si—N bond in the precursor is catalytically effected in the presence of hydrogen or a hydrogen donor, and the cleavage product is then caused to react with a second cleavage product or with a compound containing an Si—H bond, an N—H bond, or both, to produce an initial silazane product having at least one newly formed Si—N bond.

In what will sometimes hereinafter be referred to as the type (b) reaction, one or more reactants are provided which in combination contain an Si—H bond and an N—H bond, and reaction is caused to occur between the two bonds in the presence of a transition metal catalyst, whereby an initial silazane product is provided having at least two Si—N bonds, at least one of which is newly formed.

The "initial" silazane products so provided may be caused to react further, according to either the type (a) or type (b) reactions, or both, simultaneously or sequentially. These reactions may include reaction with other M—H bonds where M is, for example, B, Al, Ga, In, Ge, Pb, S, or Sn.

A. Preparation of Precursor Materials

The precursor material may be monomeric, oligomeric or polymeric, and, in addition to at least one Si—N and/or Si—H bond, may contain one or more Si—Si, Si—C, Si—O, or N—H bonds. Ultimately, an Si—N bond or Si—H bond and, in some cases, one or more of the "Si—A" bonds of these precursors, wherein A is Si, C or O will be caused to break and one or more new Si—N bonds are caused to form. In general, precursors having Si—N, Si—H bonds or both are illustrated by Formulae 2 and 3:

Formula 2

Formula 3

In the above formulae, x is an integer from 0 to 4 inclusive y is an integer from 0 to 4 inclusive, z is an integer from 0 to 2 inclusive, the sum of x, y and z is 4, a is an integer from 0 to 2 inclusive, b is an integer from 0 to 2 inclusive, the sum of a and b is 2, and m is an integer defining the number of monomer units in the oligomer, polymer or copolymer. The R moieties, i.e. the substituents on the nitrogen atom(s), which may be the same or different and may form part of a cyclic or polymeric structure, are independently selected from the group consisting of: hydrogen; boryl; hydrocarbyl including lower alkyl (1-6C), lower alkenyl (1-6C), lower alkynyl (1-6C), aryl including phenyl, benzyl and the like, lower alkyl substituted aryl, cycloaliphatic; silyl or polysilyl, including silazane, siloxane, and siloxazane groups (hereinafter sometimes "silazyl", "siloxyl", and "siloxazyl"); said hydrocarbyl and said silyl functionalities being optionally substituted with amino, hydroxyl, an ether moiety or an ester moiety, lower alkoxy (1-6C), a fused aromatic radical of 8 to 20 carbon atoms, or an organometallic radical which may include elements such as B, Al, Ga, In, Ge, Pb, S, or Sn. The nitrogen may also be present in various forms such as —NH—, —NH—NH—, —NH—NR—, —N-R—NR—, —NR—R—NR—, polyamines, and the like.

The R' groups, i.e. the substituents on the silicon atom, which may be the same or different and may form part of a cyclic or polymeric structure, are independently selected from the group consisting of: hydrogen; amino; hydrocarbyl including lower alkyl (1-6C), lower alkoxy (1-6C), lower alkenyl (1-6C), lower alkynyl (1-6C), aryl including phenyl, benzyl and the like, lower alkyl substituted aryl, cycloaliphatic; silyl or polysilyl including silazyl, siloxyl, and siloxazyl; said hydrocarbyl or silyl being optionally substituted with amino, hydroxyl, an ether moiety or an ester moiety, lower alkoxy, a fused aromatic radical of 8 to 20 carbon atoms, or an organometallic radical which may include elements such as B, Al, Ga, In, Ge, Pb, S, or Sn. The silicon moiety, as above, may be present in various forms, i.e. as —SiR'$_3$, —SiR'$_2$—, —SiR'$_2$—SiR'$_2$—, polysilane, etc. Although R' may in some instances be a hydrocarbyl moiety, it is preferable for many applications that the precursor be substantially free of Si—C bonds, e.g., for the ultimate preparation of ceramic products which are substantially carbon-free.

These precursors or reactants are preferably prepared by methods as will be described and claimed herein.

Scheme VIII illustrates a preferred synthetic route used in making a monomeric precursor useful in the present method.

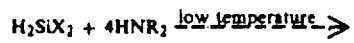

Scheme VIII $$H_2Si(NR_2)_2 + 2R_2NH_2Cl$$

In the above reaction sequence, X is a halogen substituent, preferably chloride, and the R moiety are as set forth above.

Procedurally, the halogen-substituted silane $H_2SiX_2$ is provided in a solvent, preferably a polar solvent such as tetrahydrofuran, diethyl ether, and the like, and approximately four equivalents of the di-substituted amine are gradually added. The temperature during this addition and admixture step is low, preferably maintained between about 5° C. and −30° C. The reaction mixture is slowly allowed to warm, and the aminosilane "precursor" product is isolated by any known method, e.g. by filtration and subsequent extraction.

Scheme IX illustrates the preferred method of making oligomeric or polymeric precursors containing Si—N bonds.

Scheme IX

The reaction of Scheme IX involves preparation of oligomers or polymers from halogen-substituted silanes and mono-substituted amines, X and R being defined as above for the compounds of Scheme VIII. (See Examples 1–3.) Use of the mono-substituted rather than the di-substituted amine provides an oligomeric or polymeric product rather than a monomeric species. Procedurally, the reaction is carried out as described for the monomer preparation reaction of Scheme III. Approximately three equivalents of mono-substituted amine are needed to complete the reaction (a ratio of between about 2.7:1 and 3.3:1 of $RNH_2:H_2SiX_2$ is preferred to obtain higher molecular weights). In a modified process, an excess of amine base containing no N—H bonds, e.g. triethylamine, may be added to neutralize the HCl formed during the reaction, in which case, less of the mono-substituted amine is required (e.g., between 0.9:1 and 1.1.:1 $RNH_2$:1 Si—X bond). As in the reaction of Scheme VIII, a polar solvent is preferred here as well.

The compound represented by Formula 3 is a novel composition of matter where $R' = H$, $NR_2$ or $NR$— with R as defined above, and m representing the number of monomer units in the polymeric or copolymeric structure; for $R = CH_3$, m being such that Mn is greater than about 600 D before any distillation or separation of the product.

Modification of the oligomeric or polymeric precursor represented by Formula 3 may be carried out as follows, in order to provide a copolymer which in some instances may be preferred for further synthesis or for pyrolysis. An example of such a copolymer is represented by Formula 4:

Formula 4

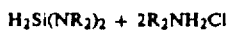

One or more compounds of formula $R^1SiX_3$ or $SiX_4$, where X is halogen and $R^1$ is preferably H but may be lower alkyl (1-6C) or aryl, e.g., phenyl or benzyl, are added to the reaction mixture to control carbon content in the form of Si—C bonds. By control of the $H_2SiX_2:R^1SiX_3:SiX_4$ mixture ratio, the $\overline{Mn}$, $\overline{Mw}$ and $\overline{Mz}$ values can be increased while maintaining tractability of the product as well as substantial linearity. In addition, a higher fraction of amine reactant $RNH_2$ is incorporated into the copolymeric product. These additional amine moieties may serve as latent reactive groups during pyrolysis. It should be noted that substantially the same result may be achieved by replacing a portion of the amine reactant $RNH_2$ with ammonia in addition to or instead of the $RSiX_3$ or $SiX_4$. Such a procedure, in conjunction with applicants' basic method of synthesizing precursor species, as outlined above, represents an improvement over known methods insofar as the molecular weight of the product is concerned.

All oligomeric or polymeric precursors represented by Formula 3 may be pyrolyzed by themselves or may be further reacted catalytically according to the reactions of either type (a) or type (b).

Suitable precursor materials for further reaction of type (a) or type (b) or both thus include alkylamines such as monomethylamine, dimethylamine, monoethylamine, hydrazine and hydrazine derivatives, polyamines, and the like, as well as a variety of silanes, silazanes, polysilazanes, siloxanes, siloxazanes, and the like. These precursors may be modified by inclusion of additional latent reactive groups such as hydrogen, amine, alkoxy, sulfide, alkenyl, alkynyl, etc., or cross-linked with suitable cross-linking reagents.

B. Formation of Silazanes

The aforementioned precursor or reactant materials may be used in either the type (a) reactions, wherein an Si—N bond is cleaved and a new Si—N bond is formed, or in type (b) reactions, wherein an Si—H moiety is caused to react with an N—H moiety so as to form a compound having a newly formed Si—N bond. Either reaction is carried out catalytically, under suitable conditions as will be outlined below.

Catalysts suitable for carrying out subsequent reaction of these precursors or reactants according to reactions of either type (a) or type (b) as described above are any type of transition metal catalysts such as those indicated in Table I, below, which are homogeneous catalysts that either dissolve in the reactants or in a solvent used to dissolve the reactants. Heterogeneous catalysts such as those of Table II may also be used or mixtures of homogeneous catalysts and/or heterogeneous catalysts. (It should be pointed out here that the "homogeneous" and "heterogeneous" classifications are made herein on the basis of solubility in organic solvents. However, it is not uncommon that during the reactions, homogeneous catalysts may be converted into a heterogeneous form and vice versa.) These catalysts may include any number of ligands, including amino, silyl and organic ligands, as discussed below and as illustrated in Tables 1 and 2.

Preferred catalysts are transition metals, and in particular the transition metals of Group VIII. Especially preferred catalysts are palladium catalysts, e.g. of the formula Pd, $PdX_2$, $L_2PdX_2$ or $L_4Pd$, where X is an anionic species such as a halide, and L is a covalent ligand, which may be organic, phosphine, arsine, amine, nitrile, and may additionally include silicon substituents. Examples are $PdCl_2$, $Pd(OAc)_2$, $(\phi CN)_2PdCl_2$ and Pd/C. As demonstrated in Example 30, these catalysts provide initial reaction rates on the order of fifteen to fifty times faster than that achieved with standard catalysts such as $Ru_3(CO)_{12}$ and $Rh_6(CO)_{16}$ under the same conditions.

The catalyst(s) may be supported on a polymer, inorganic salt, carbon, or ceramic material or the like. The heterogeneous catalyst may be provided in a designed shape, such as particles, porous plates, etc.

The catalyst can be activated by heating alone or by concurrent treatment of the reaction medium with particulate or nonparticulate radiation. The catalyst may also be activated by promoters such as acids, bases, oxidants or hydrogen, or may be stabilized by reagents such as amines, phosphines, arsines and carbonyl. The concentration of catalyst will usually be less than or equal to about 5 mole % based on the total number of moles of reactants, usually between about 0.1 and 5 mole %. In some instances, however, catalyst concentration will be much lower, on the order of ppm.

Table 1, Homogeneous Catalysts $H_4Ru_4(CO)_{12}$, $Fe(CO)_5$, $Rh_6(CO)_{16}$, $Co_2(CO)_8$, $(Ph_3P)_2Rh(CO)H$, $H_2PtCl_6$, nickel cyclooctadiene, $Os_3(CO)_{12}$, $Ir_4(CO)_{12}$, $(Ph_3P)_2Ir(CO)H$, $NiCl_2$, $Ni(OAc)_2$, $CP_2TiCl_2$, $(Ph_3P)_3RhCl$, $H_2Os_3(CO)_{10}$, $Pd(Ph_3P)_4$, $Fe_3(CO)_{12}$, $Ru_3(CO)_{12}$, transition metal hydrides, transition metal salts (e.g., $ZnCl_2$, $RuCl_3$, $NaHRu_3(CO)_{11}$) and derivatives, $PdCl_2$, $Pd(OAc)_2$, $(\phi CN)_2PdCl_2$, and mixtures thereof.

Table 2, Heterogeneous Catalysts

Pt/C, $Pt/BaSO_4$, Cr, Pd/C, Co/C, Pt black, Co black, Ru black, Ra—Ni, Pd black, $Ir/Al_2O_3$, $Pt/SiO_2$, $Rh/TiO_2$, $Rh/La_2O_3$, Pd/Ag alloy, $LaNi_5$, $PtO_2$, and mixtures thereof.

The reaction is carried out in solution with the solvent comprising either the reactants themselves or an added nonreactive organic solvent such as a hydrocarbon, an ether (e.g., ethyl ether, tetrahydrofuran), a halogenated hydrocarbon ($CHCl_3$, $CH_2Cl_2$, $ClCHF_2$, $ClCH_2CH_2Cl$, an aromatic such as benzene, toluene, or methylphenyl ether, or a polar solvent such as acetonitrile, pyridine, or a tertiary amine. Some reactions may, if desired, be carried out in the gas phase by flowing the reactant(s) over a metal catalyst.

Mild temperatures that will activate the catalyst are typically used. Such temperatures will normally be in the range of −78° C. to 250° C. Higher temperatures are necessary especially where steric hindrance is a problem. In general, higher temperatures provide for a faster reaction, but will result in a greater degree of cross-linking. Type (b) reactions require a lower temperature than type (a) reactions, generally, as cleavage of the Si—N bond in the type (a) reactions requires a higher activation energy.

Where the reaction is of type (a) (cleavage of an Si—N bond and formation of a new Si—N bond, i.e. rearrangement or metathesis reactions), the reaction is carried out in the presence of hydrogen or a hydrogen donor. Suitable hydrogen donors include silicon hydrides, metal hydrides optionally activated with a proton source, alcohols, amines, mono-, di- and tri-alkylamines, tetralin, tetrahydroquinoline, and the like.

In type (a) reactions, the cleavage product reacts with a compound containing an Si—H bond, an N—H bond, or both, to form an initial silazane product having at least one newly formed Si—N bond. In type (b) reactions, one or more reactants which in combination contain an Si—H and an N—H bond are caused to react. In both of these reactions, the compound containing the N—H bond may be ammonia, $RNH_2$, $R_2NH$, with R as defined above, for precursor compounds. One or more compounds containing an M—H bond may also be present, wherein M is, for example, B, Al, Ge, In, Ga, Pb, S, or Sn, which reacts with either the cleavage product of type (a) reactions or with a reactant in type (b) reactions.

In reactions of type (b), the Si—H and N—H bonds which are caused to react may be in the same compound, causing cyclization or polymerization, or they may be in two or more different compounds.

Examples of type (a) reactions thus include the following:

Scheme X

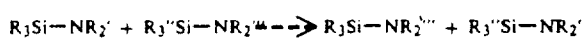

Scheme XI

Scheme XII

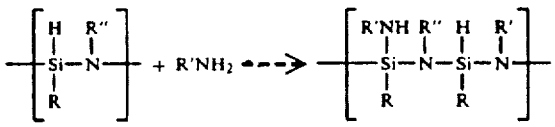

Scheme XIII

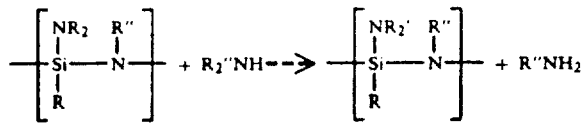

Examples of type (b) reactions include:

Scheme XIV

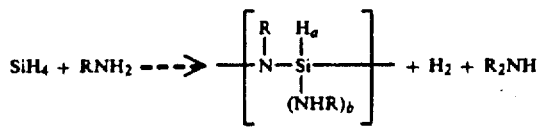

Scheme XV

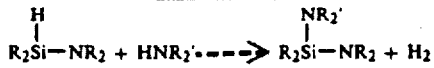

Scheme XVI

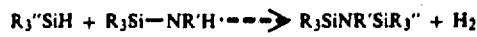

Scheme XVII

-continued

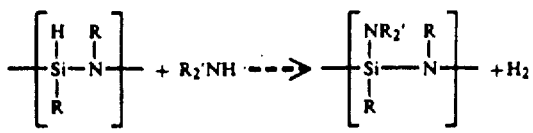

After an initial reaction according to type (a) or type (b) (or both), further reaction of the initial silazane product(s) may result, by lapse of time, type of catalyst, amount of catalyst, choice of solvent, increase in temperature, or addition of further reactive species. During the reaction process, or after completion thereof, the low and high molecular weight fractions may be separated by size exclusion chromatography, ultrafiltration, membrane separation, distillation, or partial precipitation techniques. Either fraction so obtained may be recycled through the type (a) or type (b) reaction sequence again. For example, the low molecular weight fraction can be further reacted so as to yield another crop of high molecular weight polymers.

A variation of the type (b) reaction is where ammonia is reacted with a compound of formula $R_3'SiH$, with $R'$ as given above:

Scheme XVIII

Polysilazanes prepared by the method of the present invention may be provided as preceramic polymers having a molecular weight far higher than that achieved by the prior art. Previously, tractable polysilazanes having molecular weights only as high as about $\overline{Mn}$ 10,000 D ($\overline{Mw} \sim 16,000$ D, $\overline{Mz} \sim 40,000$ D) were known, and these polymers displayed a number of problems with regard to volatility, purity, cross-linking, molecular structure, carbon content, etc. By contrast, tractable polymeric silazanes having much higher molecular weights have been achieved with the present method (see Example 23). Thus, the invention herein encompasses compositions of matter having the recurring structure

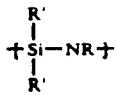

Formula 5 wherein R and R' are as defined above for the nitrogen and silicon substituents, respectively, wherein the polymer is tractable and wherein $\overline{Mn}$ is higher than about 10,000 D, preferably higher than 20,000 D, the $\overline{Mw}$ is higher than about 16,000 D, preferably higher than about 32,000 D, $\overline{Mz}$ is higher than about 40,000 D, preferably higher than about 80,000 D or combinations thereof, and the overall polymer distribution provided contains compounds with molecular weights greater than about 50,000 D, preferably greater than about 500,000 D as observed by, e.g., size exclusion chromatography. These $\overline{Mn}$, $\overline{Mw}$ and $\overline{Mz}$ values are given for the polymer distribution obtained directly without any separation or distillation step. Polysilazanes containing the repeating unit [$H_2SiNCH_3$] in the polymer or the copolymer having $\overline{Mn}$ greater than about 600 D before vacuum distillation of volatile compounds and greater than about 800 D after distillation or with $\overline{Mw}$ greater than 2000 D or $\overline{Mz}$ greater than about 4000 D or combinations thereof are also new compositions of matter. "N" and "Si" may represent polyamino or polysilyl structures as outlined above.

The invention also encompasses novel silazane structures prepared by the reactions of type (a) and type (b) wherein a precursor or reactant has at least one Si—N bond and an Si—H bond or an N—H bond or both, and the reaction product has at least two different types of Si—N bond species, wherein an "Si—N bond species" (i.e., two nonidentical structures) is defined as an $R'_3Si$—$NR_2$ moiety with R and R' as given earlier. Novel compounds are also prepared by the reaction of silane or a mono-substituted silane ($R'_3SiH_3$) with an $NHR_2$ compound.

The invention further includes novel siloxazane oligomers and polymers which include the structure R"—[—O—Si—N]. These can be prepared from siloxane precursors, i.e. precursors having one or more Si—O and two or more Si—H bonds, according to the method outlined as type (b). The following scheme illustrates the various ways in which polysiloxazanes may be prepared according to the method of the present invention.

Scheme XIX

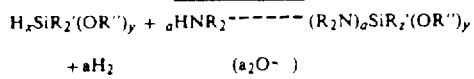

Scheme XX

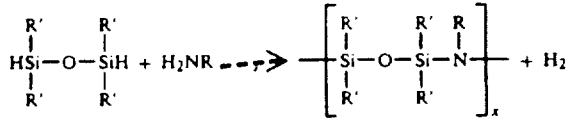

Scheme XXI

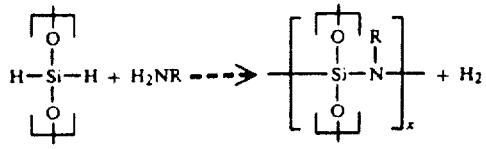

Scheme XXII

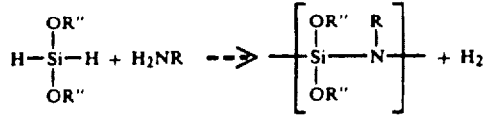

Scheme XXIII

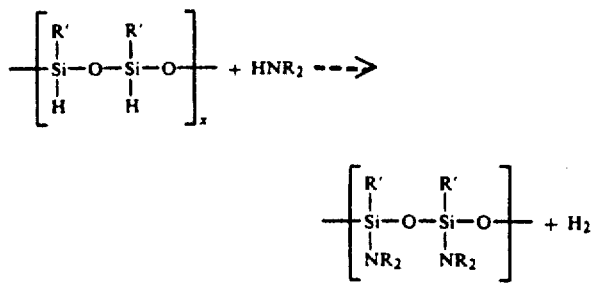

Novel siloxanes as provided herein are of the general structure

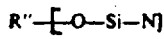

wherein R″ is silyl or hydrocarbyl. More specifically, novel siloxazane monomers are of the structure

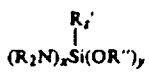  Formula 6 wherein x is an integer from 2 to 3 inclusive, y is an integer from 1 to 2 inclusive, z is an integer from 0 to 1 inclusive, R and R' are as given above and R″ is in this case defined as R but excludes amino and alkoxy substituents. Novel polysiloxazanes also include oligomeric and polymeric species, which are given by

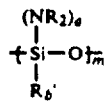  Formula 7 wherein a is an integer from 0 to 2 inclusive, b is an integer from 0 to 1 inclusive, the sum of a and b is 2, m is an integer defining the number of monomer units in the compound, and R and R' are as given above. If desired, high molecular weight polysiloxazanes, having $\overline{Mn} \geq 10,000$ D, preferably $\geq 20,000$ D, $\overline{Mw} \geq 16,000$ D, preferably $\geq 32,000$ D, or $\overline{Mz} \geq 40,000$ D, preferably $\geq 80,000$ D or combinations thereof, may be obtained by the methods outlined above. Synthesis of these compounds is carried out according to the type (b) reaction sequence.

C. Pyrolysis to Ceramic Materials

Another important advantage of the compositions and methods of the present invention is the specificity and degree of ceramic yield upon pyrolysis. For example, the high molecular weight polysilazanes display a correspondingly high ceramic yield, the ceramic materials so provided having a high silicon nitride content if desired. Silicon nitride may be provided with purity higher than about 80% upon pyrolysis of the polysilazanes provided herein when pyrolysis is conducted under nitrogen, argon or other inert atmosphere, or higher than about 95% upon pyrolysis of the polysilazanes in an ammonia or other amine atmosphere. Carbon-free polysilazanes which may be prepared according to the method herein may provide silicon nitride of even ͺher purity, i.e. 98–99% or higher.

Similarly, high ceramic yields of silicon oxynitride ($Si_2ON_2$) mixtures may be obtained upon pyrolysis using the methods described herein. The novel methods represent a significant advance in the art, as known synthetic procedures for making silicon oxynitride, a desirable ceramic material having refractory properties of both oxides and nitrides, are problematic. Two novel pathways for production of silicon oxynitride are provided herein.

In the first of these, siloxane oligomers or polymers such as $[CH_3SiHO]_x$ can be reacted with ammonia or amine to introduce nitrogen moieties into these species (see, e.g., Schemes XIX–XXIII). These reactions can lead to the formation of a nitrogen cross-linked polymer having a homogeneous distribution of Si—O and Si—N bonds in the polymer. The siloxazane so provided may be pyrolyzed under an inert gas such as nitrogen or argon, or under ammonia or a gaseous amine compound, to yield ceramic mixtures containing silicon oxynitride.

Alternatively, nitrogen-free siloxane starting materials which may be oligomeric or polymeric are pyrolyzed under ammonia or a gaseous amine atmosphere to give silicon oxynitride directly. In this case, the nitrogen is introduced into the siloxane during rather than prior to pyrolysis. The siloxane may be a sesquisiloxane ($[R'SiO_{1.5}]_n$), a polyhydridosiloxane (Formula 8) or a cross-linked polysiloxane (Formula 9) or a polysiloxane with latent reactive groups (Formula 8) such as hydrogen amine, alkoxy, sulfide, alkenyl, alkynyl, etc., which can be cross-linked during heating or replaced during curing.

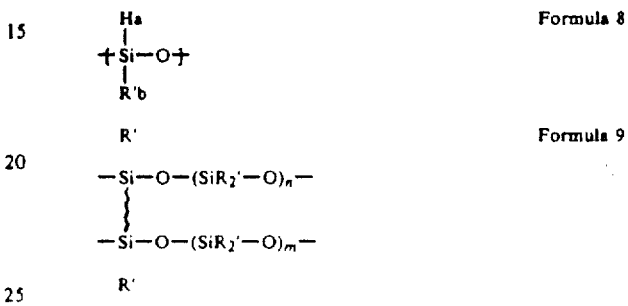

In the above formulae, a, b, and R' are defined as for Formula 3.

If desired, silicon carbide, also, may be prepared in high yield upon pyrolysis, using polyhydridosiloxane-based preceramic polymers and selected pyrolysis conditions. The common method for production of SiC fine powder is a high temperature reaction between silica and carbon powders, although more recently, SiC powders have been prepared by pyrolysis of sesquisiloxanes (see, e.g., Fox et al., "Better Ceramics through Chemistry" Symposium, J. Brinker, Ed.; Mat. Res. Soc. (1986), in press). The present method provides an inorganic polymer-controlled route to silicon carbide fine powders and coatings which are more homogeneous than previously obtained and a process by which the composition of the product and the amount of cross-linking therein can be carefully controlled. This method decreases the oxygen content of the the previous method in the polymeric precursor, leading to higher purity SiC powders.

The general procedure described above in type (b) reactions can be used to prepare preceramic polyhydridosiloxanes, e.g. by cross-linking siloxane precursors with amines such as monoalkylamines, ammonia, hydrazine, and the like, using Si—H catalytic activation. In alternative embodiments, other cross-linking agents such as water, diols, ethers, sulfides, alkenyl, alkynyl, and dienoic compounds may be used, as can organic substituents (e.g., lower alkyls) modified with latent reactive groups such as amines, hydroxides, alkoxides, sulfides, ethers, etc., also using an Si—H catalytic activation method.

Procedurally pyrolysis, according to the preferred method of the present invention, is carried out as follows. A polysilazane, polysiloxazane or polysiloxane is heated in an inert atmosphere such as in nitrogen or argon, or in an ammonia or amine atmosphere, at a predetermined heating rate. As will be demonstrated in Examples 31 and 32, the heating rate during pyrolysis is strongly correlated to the yield of ceramic material obtained. Preferred heating rates for bulk pyrolysis are between about 0.1° C. and 10.0° C. per minute, preferably between about 0.5° C. and 2.0° C. per minute, with a particularly effective heating rate, optimizing ceramic yield, of about 0.5° C. per minute. In some applications, however, flash pyrolysis may be preferred. The temperature of the polymer is typically raised to between about 500° C. and about 900° C., optionally higher, to about 1600° C.-1800° C., to provide sintering or grain growth of the ceramic material. The heating process may include one or more isothermal holding steps, in order to control the pyrolysis, to provide more cross-linking at moderate temperature (less than about 400° C.) and to further increase the yield of the final product. If desired, pyrolysis may be carried out in the presence of a catalyst; examples of suitable catalysts are set forth in Tables I and II.

Optionally, pyrolysis may be carried out only partially, i.e. in applications where it is not necessary to obtain a fully pyrolyzed material. Such applications include coatings, siloxazane or silazane rubbers, glasses, etc., or where the substrate can be damaged by high temperatures. Such "partial pyrolysis" or partial curing may be carried out at temperatures lower than 500° C.

Depending on the preceramic polymer pyrolyzed, then, the ceramic products may include silicon nitride, silicon carbide, silicon oxynitride, silicon nitride/silicon carbide alloys, silicon nitride/boron nitride alloys, silicon carbide/boron nitride alloys, and mixtures thereof.

D. Ceramic Coating Procedures

The ceramic materials provided herein are useful in a number of applications, including as coatings for many different kinds of substrates.

Silicon nitride and silicon oxynitride coatings may be provided on a substrate, for example, by a variation of the pyrolysis method just described. A substrate selected such that it will withstand the high temperatures of pyrolysis (e.g., metal, glass, ceramic, fibers, graphite) is coated with a preceramic polymer material by dipping in a selected silazane or siloxazane polymer solution, or by painting, spraying, or the like, with such polymer solution, the solution having a predetermined concentration, preferably between about 0.1 and 100 wt. %, more preferably between about 5 and 10 wt. % for most applications. The polymer is then pyrolyzed on the substrate by heating according to the pyrolysis procedure outlined above. In such a method, pyrolysis can be conducted relatively slowly, i.e. at a heating rate between about 0.1° C. and 2.0° C. per minute, in order to allow evolved gas to escape without forming bubbles in the coating, and can include one or more isothermal holding steps. In some instances, for example with relatively temperature-sensitive materials, or where a rapid-coating process is desired, a flash pyrolysis step may be preferred. Repeated, multiple coatings may be applied where a thicker layer of material is desired, with partial curing or gradual or flash pyrolysis following each individual coating step.

The pyrolysis temperature will vary with the type of coating desired. Typically, temperatures will range from about 350° C. to about 1100° C. Lower temperatures, below about 500° C., can result in only partially pyrolyzed polymer, as discussed in Section C.

Optionally, the liquid or dissolved polymer may be admixed with ceramic powders such as silicon nitride or silicon carbide optionally admixed with sintering aids such as aluminum oxide, silica, yttrium oxide, and the like, prior to coating. Cross-linking agents as set forth in Section C may be included in the coating mixture as well.

The above coating procedure is a substantial improvement over the conventional, chemical vapor deposition (CVD) method of producing silicon nitride coatings in which the appropriate compounds (e.g., $SiH_4$ and $NH_3$ or volatile silazane) react in the vapor phase to form the ceramic which deposits on the target substrate. CVD is typically an inefficient, time-consuming process which requires costly and specialized equipment. The procedure described above for producing coatings containing silicon nitride can be done with a conventional furnace. Further, the method leads to heat-stable, wear-, erosion-, abrasion, and corrosion-resistant silicon nitride ceramic coatings. Because silicon nitride is an extremely hard, durable material, many applications of the coating process are possible. One specific application is in gas turbine engines, on parts which are particularly susceptible to wear. Also, because silicon nitride is an insulator, the coating process could be used as the dielectric material of capacitors, or for providing insulating coatings in the electronics industry. Other applications are clearly possible.

In an alternative embodiment of the invention, a substrate is spray-coated with ceramic or preceramic materials. Such a procedure provides for a higher density coating, as well as for a greater degree of homogeneity. Preceramic coatings may be provided on a substrate, or at higher temperatures, one or more ceramic coatings may be provided. Gaseous species, such as silane and ammonia, which are capable of reacting to form preceramic polymers, are introduced into a nozzle. The gases are admixed within the nozzle and passed over a transition metal catalyst bed contained within the nozzle, suitable transition metal catalysts herein are selected from those set forth in Tables I and II. The catalyst bed initiates the formation of preceramic materials from the gaseous species. At the nozzle, the gaseous preceramic materials are mixed with inert or reactive gases introduced into the apparatus through one or more inlets, and the substrate surface is coated with a mixture of these materials. Such a procedure, which provides a suspension of liquid preceramic materials in air, may be used for the preparation of fine powders, as well.

The desired polymerization reaction designated herein as type (a) or type (b) thus takes place as the gases are passed over the catalyst bed. The inert gas delivers the preceramic materials to the substrate surface, or, if the gas phase is heated, it can deliver actual ceramic powders or mixtures of powders and preceramic polymer having controlled-size particles. The process can be used to form ultrafine aerosols of precursors and homogeneous catalyst solutions for ultrafine particle applications.

E. Fabrication of Molded Ceramic Bodies

The preceramic polymers as provided herein, admixed with ceramic powders, may be used to form three-dimensional articles by injection- or compression-molding. In a preferred embodiment of the invention, a preceramic polymer/ceramic powder system is used to form three-dimensional bodies by compression molding. The inventors herein have surprisingly discovered that there is chemical or physical interaction between the novel polysilazanes or polysiloxazanes and a ceramic powder which includes $Si_3N_4$ at temperatures as low as 800° C. Such chemical or physical reactions are not expected because even ultrafine-grained $Si_3N_4$ powder containing sintering aids does not sinter at such low temperatures. After heating at 800° C. in $N_2$, cylindrical pellets containing both silicon nitride and polysilazane show volume shrinkage of up to 5% and considerable mechanical strength, while pellets of dry powder with no polymer added, heated under the same conditions, show neither shrinkage nor enhanced mechanical strength relative to a powder compact pressed at room temperature. This aspect of the invention exploits the discovery of this chemical interaction to produce ceramic bodies which can have, if desired, a very low pore volume. By using carefully selected conditions, three-dimensional ceramic forms can be prepared which have a green density of about 85% (or a pore volume of 0.06 cm$^3$/g or less). (If desired, however, lower density materials can be made by the same process; see Examples 35–43.)

A polymer solution containing a polysilazane, e.g., [H$_2$SiNCH$_3$]$_x$, polysiloxane, or polysiloxazane is prepared and mixed with a ceramic powder composition comprising, for example, silicon nitride, sintering aids such as yttrium oxide; aluminum oxide; and silica and, optionally, fibers and whiskers of, for example, silicon nitride, silicon carbide, or carbon. The composition of the polymer/powder mixture is such that it contains between about 5 and about 50 wt. % polymer, and correspondingly, between about 50 and about 95 wt. % ceramic powder. The mixture is loaded into a suitable form and compression molded at between about 25,000 and about 50,000 psi. The formed body is then heated under an inert gas (or under ammonia or a gaseous amine compound) at a temperature between about 500° C. and about 900° C. to convert the polymer to ceramic material. The body is then sintered at a temperature of at least about 1600° C. at a pressure of at least about 3 atm N$_2$ or other gas in order to provide a very dense, substantially nonporous material. The results as demonstrated in the examples indicate that the procedure may also be successful in the absence of sintering agents.

F. Preparation of Fibers

The polymers provided in the present invention, and the substantially linear high molecular polysilazanes in particular, can be used for preceramic fiber spinning.

Three general spinning techniques are commonly used: (a) melt spinning, in which the polymer is spun from its melt and solidified by cooling; (b) dry spinning, in which the polymer is at least partially dissolved in solution and pulled out through the spinneret into a heat chamber, then solidified by solvent evaporation; and (c) wet spinning, in which a concentrated polymer solution is spun into a coagulation or regeneration bath containing another solvent in which the polymer is not soluble. These methods are suitable for tractable high molecular polysilazanes having $\overline{Mn} \geq 10,000$ D or $\overline{Mw} \geq 16,000$D or $\overline{Mz} \geq 40,000$D or combinations thereof, or containing a polymeric species in the resultant polymer distribution having a molecular weight over 50,000D. While these polymers may be either meltable, malleable, or soluble in some types of solvents, they may be insoluble in others (e.g., for wet spinning).

Additional relatively small quantities (0.1–5.0 wt. %) of a very high molecular weight substantially linear organic polymer (100,000–5,000,000 D) may be mixed with the inorganic polymer to support and improve the fiber strength after spinning, as taught in, e.g., U.S. Pat. Nos. 3,853,567 to Verbeek and 3,892,583 to Winter et al.

The supporting technique is especially useful when low molecular weight and/or nonlinear polymers having a very low degree of chain entanglement are used.

One problem encountered in ceramic fiber fabrication derives from the fusability of inorganic polymers during pyrolysis. This fusability results in structural problems in the spun fiber. Polymers produced by the present invention, however, overcome the fusability problem, providing that the catalytic process as described herein is actually incorporated into the fiber-spinning process. For example, a high molecular weight polysilazane may be mixed with homogeneous catalyst and heated in the spineret or in the curing chamber to cause reactions of type (a) or (b) or both to occur and increase the degree of cross-linking in the fiber. Alternatively, the spineret can itself be a catalytic bed. Cross-linking agents such as those set forth in Section C may also be included in the fiber-spinning process to provide additional cross-linking; similarly, latent reactive groups (e.g., free amino moieties) may be present, as well, for the same reason, even in the absence of catalyst.

G. Other Applications

Many other applications of the novel polymers of the invention are clearly possible.

The results summarized in part G, for example, suggest combination of polysilazanes, polysiloxazanes, and related compounds with other ceramic powders (e.g., SiC, BN, B$_4$C) to produce composite articles. Such a composite of, e.g., a siloxazane polymer/SiC powder mixture may give an article having improved oxidation resistance. Another application would be to use the novel polymers in dissolved or liquid form as binders combined with ceramic powders so as to provide a fluid polymer/powder mixture.

Infiltration and impregnation processes are additional possibilities, as discussed, for example, in U.S. Pat. No. 4,177,230 to Mazdiyasni et al. and in W. S. Coblenz et al. in *Emergent Process Methods for High-Technology Ceramics*, ed. Davis et al. (Plenum Publishing, 1984). Two general methods are typically used. One is a high-vacuum technique in which a porous ceramic body is contacted under vacuum with a liquid or dissolved preceramic polymer. After a high vacuum infiltration, the article is pyrolyzed to achieve a higher density. The second method is high-pressure infiltration. Either of these methods can be adapted for the polymers of the invention. In addition, low molecular weight oligosilazane solutions having higher mobility in the porous ceramic body can be incubated with the ceramic body and a transition metal catalyst, followed by curing of the oligomeric reactants to obtain reactions of type (a) or (b) or both. In situ chain extension or cross-linking will reduce the mobility and volatility of the oligomeric starting materials.

Other applications of the novel polymers include use as a cement to "bond" ceramic materials such as powders, ceramic fibers, and three-dimensional forms. Bonding of fibers followed by pyrolysis can yield matrices or matrix composites. In some application, ceramic articles may be joined by the polymers, under pressure, followed by pyrolysis. The chemical interactions discussed in part F between the polymer and ceramic powders may occur in bonding to enhance the strength of the cement.

It is to be understood that while the invention has been described in conjunction with the preferred specific embodiments thereof, that the foregoing description as well as the examples which follow are intended to illustrate and not limit the scope of the invention, which is defined by the scope of the appended claims. Other aspects, advantages and modifications within the scope of the invention will be apparent to those skilled in the art to which the invention pertains.

EXAMPLES

Experimental: Unless otherwise indicated, the reagents used were obtained from the following sources: silanes, from Petrarch Systems, Inc., Bristol, Pa.; organic reagents including amines, from Aldrich Chemical Col, Milwaukee, Wis.; gases, from Matheson, Seacaucus, N.J.; and catalysts, from Strem, Newburyport, Mass.

EXAMPLE 1
Precursor Formation

Into a flame-dried three-neck flask equipped with an overhead mechanical stirrer and an $N_2$ inlet was placed 500 ml anhydrous ether. This was cooled to $< -70°$ C. in a dry ice/acetone bath. Dichlorosilane (150 g; 1.5 moles) was then condensed into the flask. An excess of $\approx$198 g (4.5 moles) monoethylamine was then added over a two-hour period. The reaction mixture was stirred for an additional four hours, and the flask was then allowed to warm slowly overnight to room temperature. The contents were diluted with 500 ml ether and filtered to remove monoethylamine hydrochloride salt.

The solids were then placed in a 2 l Erlenmeyer flask and stirred for 10 minutes in 500 ml boiling THF. The mixture was filtered hot. The extraction was repeated and the solids were rinsed with an additional 500 ml hot THF. 89.0 g of products were obtained after solvent removal (81% yield) with $\overline{Mn}=490$ D; $\overline{Mw}=1,720$ D; $\overline{Mz}=11,370$ D. Fractionation by high vacuum distillation (150°/300μ) gives 60% of volatile products having $\overline{Mn}$ of 307 D and 40% residue with $\overline{Mn}=420$ D, $\overline{Mw}=2670$ D, and $\overline{Mz}=17,560$ D.

EXAMPLE 2
Precursor Formation

Into a flame-dried three-neck flask equipped with an overhead mechanical stirrer and an $N_2$ inlet was placed 500 ml anhydrous ether. This was cooled to $< -70°$ C. in a dry ice/acetone bath. Dichlorosilane (150 g; 1.5 moles) was then condensed into the flask. An excess of $\approx$300 ml monomethylamine was then added over a two-hour period. The reaction mixture was stirred for an additional two hours. The flask was then allowed to warm slowly overnight to room temperature. The contents were diluted with 500 ml ether and filtered to remove monomethylamine hydrochloride salt. The solvent fractions were evaporated under reduced pressure to yield 10-20 g (11-23%) of oil.

The low yield was attributed to poor extraction of the solids, as the weight of the solids was much higher than expected.

An improved method for the solid cake extraction was developed. The reaction mixture was filtered and the solids rinsed with ether and THF. The solids were then placed in a 2 l Erlenmeyer flask and stirred for 10 minutes in 500 ml boiling THF. The mixture was filtered hot. The extraction was repeated and the solids were rinsed with an additional 500 ml hot THF. With this extraction method followed by solvent evaporation the yield improved to 60-75%. The viscous oligomers obtained after evaporation of the solvent had normal average molecular weight ($\overline{Mn}$) of $\overline{Mn}=800$-1250 D. More than 85-95% of original product material remained after high vacuum distillation (150° C./300μ) having $\overline{Mn}=1400$ D and higher. Soxhlet extraction can be used for the above cake extraction.

EXAMPLE 3
Precursor Formation (Modified)

Into a flame-dried three-neck flask equipped with an overhead mechanical stirrer and an $N_2$ inlet was placed 1 l anhydrous ether. This was cooled to $< -70°$ C. in a dry ice/acetone bath. Dichlorosilane (154 g; 1.5 moles) was then condensed into the flask. Trichlorosilane, $SHCl_3$, 15.4 g (0.11 mole), was added into the reactor. An excess of $\approx$400 ml monomethylamine was then bubbled into the solution over a three hour period. The reaction mixture was stirred for an additional two hours. The flask was allowed to warm slowly overnight to room temperature. The contents were then diluted with 500 ml ether and filtered to remove monomethylamine hydrochloride salt.

The solids were then placed in a 2 l Erlenmeyer flask and stirred for 10 minutes in 500 ml boiling THF. The mixture was filtered hot. The extraction was repeated and the solids were rinsed with an additional 500 ml hot THF. An excess of 20 ml monomethylamine was bubbled through the extracted solution at room temperature to complete removal of chloride impurities. The cloudy solution was then filtered, followed by evaporation of solvent. The 89 g of oligomers obtained after evaporation of the solvent had $\overline{Mn}=1,780$ D, $\overline{Mw}=7,460$ D, and $\overline{Mz}=28,020$ D. No distillation or purification was necessary.

EXAMPLE 4
Reaction of Diethylsilane with Ammonia

To 20.0 mmole of diethylsilane (1.76 g) were added 25 μmol of $Ru_3(CO)_{12}$ (16 mg). The solution was heated at 60° C. under approximately 80 psi of $NH_3$. After 1 hour, 85% of the silane was converted to a mixture of oligomers and the pressure increased by 200 psi due to $H_2$ evolution. Although $Et_2SiH_2$ disappeared totally after 2 hours, chain oligomerization and cyclization continued for 12 hours. Oligomers of types A ($n=3-5$; major), B ($n=1-4$; major), C ($n+n'=2$ or 3), and D ($n+n'+n''+n'''=2$) were found in the product mixture. Small quantities of other series—$H[Et_2SiNH]_nH$ ($n=2-4$) and $H_2N[Et_2SiNH]_nH$ ($n=2$) also appeared in the solution.

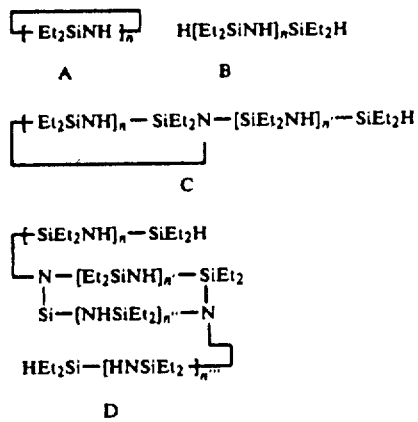

Thus, while some cyclomers were produced, most of the products were substantially linear oligomers.

EXAMPLE 5

Reaction of TMDS with Ammonia

To 30 mmole of tetramethyldisilazane (TMDS) were added 25 μmol of Ru$_3$(CO)$_{12}$. The solution was heated at 135° C. under 80 psi of NH$_3$. TMDS disappeared totally after 20 h and polymerization continued for 28 h. The polymeric residue (heavy oil) was 2.44 gm (yield 61 wt %) after distillation at 180°/0.3 mm Hg, with an Mn of 764 D. The major polymeric series was the linear HSiMe$_2$[NHSiMe$_2$]$_x$NHSiMe$_2$H. Smaller, branched chain polymers appeared as well. Molecular weights greater than 26000 D can be obtained by varying of reaction conditions.

EXAMPLE 6

Reaction of TMDS with Ammonia and Hydrazine

To 20 mmole of TMDS were added 25 μmol of Ru$_3$(CO)$_{12}$. The solution was heated at 135° C. under 100 psi of NH$_3$. The conversion of TMDS was 94% after 1 h. 0.1 g of hydrazine were added and the solution was heated again for 3 hours. The GC results showed that most of volatile products disappeared. The high polymeric residue was 68 wt % after distillation at 180° C./0.3 mm Hg. Similar results are achieved by using 200 mg of 5% Pt/C (activated under H$_2$) using identical conditions. The number average molecular weight ($\overline{Mn}$) is 1200 D.

EXAMPLE 7

Reaction of TMDS with Ammonia

To 75 mmole of TMDS were added 25 μmol of Ru$_3$(CO)$_{12}$ and the solution was heated at 135° C. under 60 psi of ammonia. The hydrogen pressure produced in the reaction was released every 1 hour and the reactor was charged again with 60 psi of NH$_3$. TMDS disappeared after 5 h. The initial turnover frequency (TF) for TMDS disappearance was 260. The net total turnover number for Si—N bond production was close to 4,480 after 8 hours.

EXAMPLE 8

Reaction of TMDS with Hydrazine

To 20 mmole of tetramethyldisilazane (TMDS) and 20 mmole anhydrous hydrazine (NH$_2$NH$_2$) were added 25 μmol of Ru$_3$(CO)$_{12}$ and the solution was heated at 135° C. under nitrogen. All the TMDS disappears after 3 hours and H$_2$ pressure was obtained (TF=528). The yield of the polymeric residue after distillation of the volatile products was 75 wt. %. The number average molecular weight ($\overline{Mn}$) was 968 D.

EXAMPLE 9

Reaction of n-Hexyl Silane with Ammonia

Ten (10.0) grams of n-hexylsilane and 16 mg of Ru$_3$(CO)$_{12}$ as catalyst were heated at 60° C. under 150 psi of ammonia in a stainless steel reactor. A pressure of 300 psi was produced during the first hour. The reactor was cooled to room temperature, the pressure was released and the reactor was charged again with 150 psi of ammonia. This procedure was repeated several times. After 1 hour, 68% of the substrate disappeared (according to calculations based on NMR analysis) and the reaction slowed down. After 17 hours, only 12% of the starting material remained in the oily solution. Only a slight additional conversion was detected when the temperature was raised to 90° C. The addition of another 16 mg of Ru$_3$(CO)$_{12}$ promoted further conversion to a viscous material which appeared concurrently with the disappearance of hexylsilane. The NMR and the VPO (vapor pressure osmometry) analyses are shown in Table 3.

TABLE 3

| Time (hours) | Form of Products | Conversion[a] (%) | Unit's Ratio[b] Si—H | N—H | Mn |
|---|---|---|---|---|---|
| 1[c] | light oil | 68 | 1.28 | 0.72 | — |
| 17[c] | slightly viscous | 88 | 1.18 | 2.18 | 921 |
| 24[d] | viscous oil | 91 | 1.06 | 2.20 | 962 |
| 28[d,e] | very viscous oil | 100 | 0.70 | 1.84 | 2772 |
| 36[d,e] | wax | 100 | 0.43 | 1.83 | 4053 |

[a] Overall conversion was determined by NMR spectra in CDCl$_3$ (ppm). For n-hexylsilane: Si—H 3.52 (t, 3); C—H 1.36 (m, 8) and 0.92 (m, 5). For polysilazanes: Si—H 4.78 (m), 4.57 (m) and 4.36 (m); C—H 1.32 (m) and 0.91 (m); N—H 0.62 (m, br).
[b] Si—H and N—H unit ratios were determined by NMR using the hexyl group integration as an internal standard.
[c] At 60° C.
[d] At 90° C.
[e] After addition of 16 mg Ru$_3$(CO)$_{12}$.

The reaction mixture was analyzed by NMR and GC-MS techniques to determine types of polymer. In Table 5, possible polymer types A, B, C, D, and E are set forth with the elemental (C, H and N) analysis for each in the upper part of the table. Actual analyses of the reaction mixture after 24 and 36 h are set forth in the lower part of the table.

Certain conclusions may be drawn from Table 4, as follows:

a. The initial conversion was very fast; the initial turnover frequency for silane conversion was 2350 per hour.

b. The polymer at 24 hours contained large quantities of Si—H bonds even when the molecular weights are high. Crosslinking was therefore prevented, possibly as a result of steric hindrance.

c. At 36 hours the high integration ratio of N—H to C—H strongly suggests that there are significant quantities of the

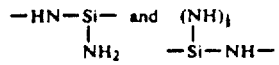

functional groups. Si—NH$_2$ was also detected by I.R. (absorbance in 1550 cm$^{-1}$ in CCl$_4$. [(NH)$_\frac{1}{2}$ signifies that the NH group was shared with another fragment of the polymer.]

d. The polymer product is believed to be a new composition of matter.

The GC-MS of the reaction solution showed a series of linear and cyclic oligomers with substituents on both the silicon, e.g., [(=N)$_3$ Si—)] and nitrogen, e.g., [(=Si)$_3$N]. The terminal Si—NH$_2$ unit was not observed in the GC-MS fragmentation patterns.

Referring to Table 4, the types of repeating units of A through E are set forth below.

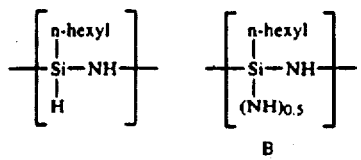

B

-continued

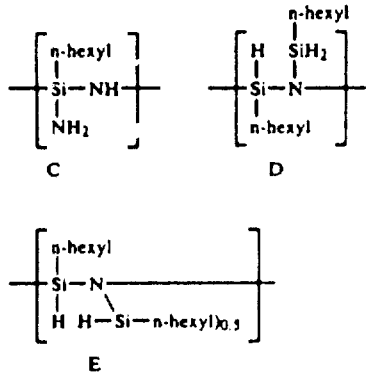

TABLE 4

| Type/hours | Elemental Analysis | | |
|---|---|---|---|
| | % C | % H | % N |
| A | 55.81 | 11.63 | 10.85 |
| B | 52.94 | 10.66 | 15.44 |
| C | 50.00 | 11.11 | 19.44 |
| D | 59.25 | 11.93 | 5.76 |
| E | 58.37 | 11.35 | 7.57 |
| 28 h | 54.51 | 10.95 | 10.84 |
| 36 h | 52.54 | 10.73 | 12.93 |

The following conclusions are drawn from Table 4. The actual analyses at 28 h conform closely to the linear type A polymer.

This example illustrates additional reaction of type (a) or type (b) following an initial such reaction, (where, here, cross-linked polymers are prepared from initially synthesized linear oligomers. The polymer obtained by this method is believed to be a new composition of matter.

EXAMPLE 10

Reaction of Phenylsilane with Ammonia

Phenylsilane (10.0 g) and Ru$_3$(CO)$_{12}$ (16 mg) were heated at 60° C. under 150 psi of ammonia in a stainless steel reactor. The reactor was cooled several times during the reaction to sample and to recharge with ammonia. After 3 hours, 84% of the phenylsilane was converted to oligomeric products (calculated from NMR data). After 14 hours, the reaction temperature was increased to 90° C., and after 18 hours 8 mg Ru$_3$(CO)$_{12}$ were added to the mixture. Table 5 summarizes the observations and the results from the NMR and VPO analyses.

TABLE 5

| Time (hours) | Form of Products | Conversion$^a$ (%) | Unit's Ratio$^b$ | | |
|---|---|---|---|---|---|
| | | | Si—H | N—H | $\overline{Mn}$ |
| 3$^c$ | slightly viscous | 84 | 1.21 | 0.98 | 549 |
| 9$^c$ | slightly viscous | 95 | 1.13 | 1.32 | -- |
| 14$^c$ | very viscous | 98 | 1.07 | 1.21 | 695 |
| 18$^d$ | hard wax | 100 | 0.98 | 1.03 | 1058 |
| 28$^{d,e}$ | solid | 100 | 0.47 | 1.47 | — |

TABLE 5-continued

| Time (hours) | Form of Products | Conversion$^a$ (%) | Unit's Ratio$^b$ | | |
|---|---|---|---|---|---|
| | | | Si—H | N—H | $\overline{Mn}$ |
| 32$^{d,e}$ | solid | 100 | 0.34 | 1.70 | 1432 |

$^a$Overall conversion was determined by NMR spectra in CDCl$_3$
$^b$Si—H and N—H unit ratios were determined by NMR using the phenyl group integration as an internal standard.
$^c$At 60° C.
$^d$At 90° C.
$^e$Addition of 8 mg Ru$_3$(CO)$_{12}$ and 2 ml of toluene (removed before molecular weight measurements).

The data for the 18 hour sample indicate the formation of linear Type E polymers (see Table 6). As additional catalyst was added and the temperature raised, more ammonia was incorporated into the polymer. After 32 h, the elemental and the NMR analyses indicate that the polymer contained units of types F, G, and H in the following approximate ratios:

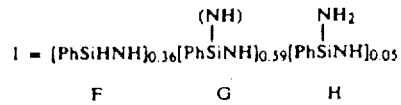

$$\mathrm{I} = [PhSiHNH]_{0.36}[PhSiNH]_{0.59}[PhSiNH]_{0.05}$$

$$\phantom{I = [}F\phantom{hSiHNH]_{0.36}[}G\phantom{hSiNH]_{0.59}[}H$$

The polymer containing units F, G and H is indicated as I above.

This solid polymer I after 32 hours was soluble in CCl$_4$, CH$_2$Cl$_2$, CHCl$_3$ and toluene. It had a glass transition point at 70°-72° C. and softened considerably at 90° C. Pyrolysis at 900° C. gave a 70% ceramic yield and finally a 35% yield when heated to 1550°. Only alpha and beta Si$_3$N$_4$ were observed by X-ray powder diffractometry although the final ceramic product contained 29% carbon (as determined by elemental analysis). The product is believed to be a new composition of matter.

TABLE 6

| Type/hours | Elemental Analysis | | |
|---|---|---|---|
| | % C | % H | % N |
| F | 59.50 | 5.78 | 11.57 |
| G | 56.25 | 5.47 | 16.40 |
| H | 52.94 | 5.88 | 20.58 |
| 18 h | 59.37 | 5.67 | 11.81 |
| 32 h | 57.42 | 5.58 | 14.21 |
| I | 57.25 | 5.60 | 14.97 |

GC-MS analysis of the mixture after 3 hours of heating revealed that majority of the oligomers (n=1-3) were type F; minor products included cyclic compounds, cyclomers with branching on a silane unit and straight and cyclic compounds branched on the nitrogen. Amine capped polymers were not observed.

EXAMPLE 11

Reaction of a Hydridosilazane

HMeN[H$_2$SiNMe]$_x$H (2.0 g; $\overline{Mn}$=560) and Ru$_3$(CO)$_{12}$ (16 mg) were heated under several reaction conditions. The results are shown in Table 7. The starting reactant $+$H$_2$SiNMe $_x$ was prepared from H$_2$SiCl$_2$ and MeNH$_2$ in ether solution as reported by Seyferth and Wiseman (Polymer Chem. Div. Preprints; Paper presented at the spring meeting of ACS, April 1984). The products were [H$_2$SiNMe]$_4$ and a linear oligomer HNMe[SiH$_2$NMe]$_x$—H (x was approximately 10).

TABLE 7

| Run | Gas Phase (atm) | Temp. (°C.) | Time (hours) | Form of Product | Ceramic Yield (%)[a] (Crystallized Form) |
|---|---|---|---|---|---|
| 1 | H₂ (1 atm) | 60 | 4 | viscous liquid (Mn - 1180; soluble in toluene and CH₂Cl₂) | 68 |
| 2 | H₂ (1 atm) | 135 | 2 | soft rubber | 75 |
| 3 | MeNH₂ (3 atm) | 60 | 4 | viscous liquid (Mn = 1200) | 78 (αSi₃N₄)[b] |
| 4[c] | NH₃ (1 atm) | 60 | 2 | hard rubber | 85 (Si₃N₄: α > β) |

[a]Pyrolyzed under N₂ by ramping the temperature to 900° C. in 6 h and then holding for 2 h at 900° C.; sintered at 1550-1600° C.
[b]Poorly crystallized.
[c]Only 8 mg of Ru₃(CO)₁₂ were used.

EXAMPLE 12

Polymerization of Ethylsilane with Ammonia

Ethylsilane, (EtSiH₃, 8 g) was condensed into a stainless steel reactor, containing Ru₃(CO)₁₂ (16 mg) in 1 ml of toluene, and cooled in a dry ice/acetone container. The reactor was then pressurized with 100 psi of ammonia (at −78° C.). A total pressure of 250 psi was obtained when the reactor was heated (o room temperature. The solution was heated at 60° C. The reactor was cooled after 1 hour to room temperature, depressurized (releasing H₂), loaded with an additional 150 psi of ammonia and reheated at 60° C. for an hour, then cycled again for 2 hours. The resulting solution (after 4 h) was very viscous. The solvent was evacuated (R.T., 0.1 mm) and the waxy polymer was heated again at 90° C. for another 2 hours to form a soft rubber. Pyrolysis of the rubber at between 200° and 900° C. gave 58% of ceramic material. The NMR and IR spectra of the polymer produced after 4 hours show the following peaks: NMR (δ, CDCl₃) Si—H (4.90-4.40, m); CH₃ (0.95, t); N—H (1.0-0.8 br); CH₂ (0.58, q). (The ratio of the Si—H to the Et—Si and N—H absorbance was 1:24 which suggests that the polymer consists of approximately 30% [EtSiHNH] units and the rest were [Et(NH₂)SiNH and [Et(NH)₀.₅SiNH]). The product is believed to be a new composition of matter.

I.R. (cm⁻¹, CH₂Cl₂), Si—NH—Si (3385, 1170, 950); Si—NH₂ (1545); Si—H (2108); Si—Et (1235, 1012).

EXAMPLE 13

Preparation of Polysiloxazane 1,1,3,3-Tetramethyldisiloxane (5.36 g, 40 mmole (HMe₂Si)₂O) and Ru₃(CO)₁₂ (32 mg, 50 μmol) were heated at 60° C. under NH₃ (150 psi). The pressure produced in the reactor was released and the reactor was recharged with NH₃ several times. 80% of the disiloxane was converted after 1.5 hours. The reaction was heated continuously for 20 hours.

GC-MS analysis indicates the following pattern:

A = [+Me₂SiOMe₂SiNH+]ₙ (n = 2-5)

-continued

B = H[+Me₂SiOMe₂SiNH]ₙSiMe₂OSiMe₂H (n = 1-6)

A 70% yield was obtained after high vacuum distillation (180° C./0.5 mm). A₍N=2₎ was isolated as solid white crystals, mp. 37° C., with a single NMR absorption at 0.12 ppm. The residue was a viscous oil with M̄n = 5690 D. (M̄n values were measured by VPO techniques. Later results indicate that VPO may be insufficient for polymers having M̄n over 2000. GPC results usually show higher values; see Example 14.)

| Elemental analysis: | % C | % H | % N | Si | O |
|---|---|---|---|---|---|
| Polymer B | 32.65 | 8.84 | 9.52 | 38.10 | 10.88 |
| Found | 32.67 | 9.10 | 8.56 | 41.89 | 7.02 |

This is an example of preparing a polysiloxazane having the general structure:

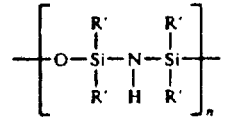

These polysiloxazanes are believed to be novel compositions of matter. R' is as defined in the text. The nitrogen may be substituted, e.g. by an organic group R, also defined earlier. The subscript n may have various values.

EXAMPLE 14

Reaction of Octamethylcyclotetrasilazane

Octamethylcyclotetrasilazane was reacted under various conditions with (+) and without (−) [(CH₃)₃Si]₂NH and with various catalysts. Results are set forth in Table 8.

Octamethycyclotetrasilazane

TABLE 8

| | | Yield of Oligomers and Polymers | | | | |
|---|---|---|---|---|---|---|
| | | | | Yield (% Weight)[c] | | |
| Run | Catalyst | [(CH₃)₃Si]₂NH | II Conv. (%)[b] | Oligomers | Polymers | M.W. |
| 1 | H₂SO₄ | − | 46 | 33 | 10 | 783 |
| 2 | H₂SO₄ | + | 46 | 18 | 33 | 587 |
| 3 | Ru₃(CO)₁₂/H₂ | − | 74 | 54 | 18 | 2551 |

TABLE 8-continued

| | | Yield of Oligomers and Polymers | | | | |
|---|---|---|---|---|---|---|
| | | | II Conv. (%)[b] | Yield (% Weight)[c] | | |
| Run | Catalyst | [(CH₃)₃Si]₂NH | | Oligomers | Polymers | M.W. |
| 4 | Ru₃(CO)₁₂/H₂ | + | 58 | 28 | 44 | 697 |
| 5 | Pt/C | − | 62 | 22 | 34 | 1080 |
| 6 | Pt/C | + | 71 | 28 | 45 | 784 |

[a]The same conditions as shown in Table 9. The reactions were carried without internal standards and the analyses were made according to the distillation of the solutions.
[b]The conversion measurement was due to the amount of cyclotetramer in the end of the reaction.
[c]Yield was in weight percentage due to the total weight of the solution. The oligomer fraction also contains the remains of disilazane (Me₃Si)₂NH.

GC-MS Analysis

Identification of polymer types produced in the reactions described in Table 8, were performed by GC-MS. This method was limited to polymers with molecular weights less than 1000. We have observed types A and B in run (1). B was the major product in run 4 (n=1-8) and A

  A

  B

Me₃SiNH[Me₂SiNH]ₙSiMe₃ appears in small quantities (n=3-7). Another set of polymers observed in even smaller quantities were C (n+n'=2-7) and D (n+n'+n''+n'''=2-6). C and D were crosslinked through nitrogen groups.

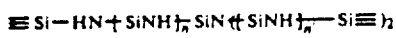  C

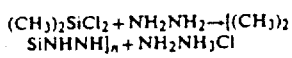  D

In the above, Si signifies —SiMe₂— and Si≡ signifies —SiMe₃.

In run 3, because of the high molecular weight, no significant products could be detected by the GC-MS. Most likely there were more crosslinks from this run which also explains the high molecular weight. Run 6 shows the same types as the parallel reaction with Ru₃(CO)₁₂ but the quantities of C and D were larger. The Pt/C catalysis without the capping agent gives series A and other quantitative series E F that indicate bi- and tri-cyclo crosslinked compounds.

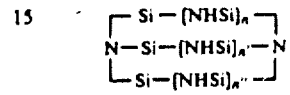  E

F contains another ring. In E, $n_{total}$ (i.e. n+n'+n'')=5-8; in F, $n_{total}$=8-9.

The polymers produced by H₂SO₄ catalysis contains types A (n=5,6), B (n=2-8; major products), and C(n=2-5) in run 2 and A (n=5-9) in run 4. In both cases the GC-MS analyses show an amount of oxygenated products in which oxygen replaced amine groups.

EXAMPLE 15

Reaction of polydimethylsilylhydrazine

To 1.8 g polydimethylsilylhydrazine H₂NNH—[Me₂SiNHNH]ₓ]—H prepared as follows:

(CH₃)₂SiCl₂ + NH₂NH₂ → [(CH₃)₂SiNHNH]ₙ + NH₂NH₃Cl ($\overline{Mn}$ ~ 1130) dissolved in 5 ml of toluene were added 25 μmol of Ru₃(CO)₁₂ and the solution was heated at 135° C. under hydrogen. The clear solution turned cloudy and viscous (at room temperature). 1.3 g of a soft solid product was obtained after distillation of the volatile products and solvent at 180° C./0.3 mm Hg. The solid had an $\overline{Mn}$ of 1220 D and started to soften at 60° C. The same treatment for the starting material in the absence of catalyst gave a slightly cloudy solution at room temperature (clear during heating). The $\overline{Mn}$ decreased to 612 D. The product was a solid after distillation and did not soften up to 250° C.

This example illustrates the use of precursors having an N—N moiety within the molecular structure.

EXAMPLE 16

Catalytic Studies

Octamethylcyclotetrasilazane was reacted with [(CH₃)₃Si]₂NH in the presence of various catalysts. The reaction conditions, catalysts and results are set forth in Table 9.

TABLE 9

| Run | Catalyst | Temp (°C.) | Time (h) | Conversion (%) | Decomposition of Catalyst |
|---|---|---|---|---|---|
| 1 | Ru₃(CO)₁₂ | 135 | 6 | 22 | s |
| 2 | Ru₃(CO)₁₂ | 180 | 15 | 80 | m |
| 3 | Ru₃(CO)₁₂/H₂ | 135 | 1 | 78 | — |
| 4 | Ru₃(CO)₁₂/H₂O | 135 | 3 | 33 | s |
| 5 | Ru₃(CO)₁₂Fe(CO)₅ | 135 | 6 | 26 | s |
| 6 | Ru₃(CO)₁₂Fe₃(CO)₁₂ | 135 | 3 | 80 | s |
| 7 | Fe₃(CO)₁₂ | 135 | 3 | 80 | s |
| 8 | Fe₃(CO)₁₂H₂ | 135 | 3 | 80 | f |
| 9 | Os₃(CO)₁₂ | 135 | — | — | — |
| 10 | Os₃(CO)₁₂ | 180 | 20 | 78 | — |

TABLE 9-continued

| Run | Catalyst | Temp (°C.) | Time (h) | Conversion (%) | Decomposition of Catalyst |
|---|---|---|---|---|---|
| 11 | $Os_3(CO)_{12}/H_2$ | 135 | 6 | 73 | — |
| 12 | $H_2Os_3(CO)_{10}$ | 135 | 3 | 78 | — |
| 13 | $Rh_6(CO)_{16}$ | 135 | 20 | 55 | s |
| 14 | $Rh_6(CO)_{16}/H_2$ | 135 | 3 | 78 | s |
| 15 | $Ir_4(CO)_{12}$ | 135 | — | — | — |
| 16 | $Ir_4(CO)_{12}$ | 180 | 15 | 70 | m |
| 17 | $Ir_4(CO)_{12}/H_2$ | 135 | 3 | 76 | f |
| 18 | Pt/C | 135 | 3 | 75 | — |
| 19 | $PtO_2$ | 180 | 15 | 25 | — |
| 20 | Pd/C | 135 | 3 | 78 | — |

Comments on Table 9 are as follows: The molar ratio of octamethylcyclotetrasilazane, silazane [$(CH_3)_3Si]_2NH$ and catalyst was 250:84:1. The reaction was carried out under hydrogen where indicated, as in Run No. 3, or with water in Run No. 4, otherwise under nitrogen. The hydrogen was at 1 atm. The time figures indicate the shortest time in which there was no further conversion of the starting silazane reactant. Butyl ether was used as an internal standard for gas chromatographic analysis. In the decomposition of catalyst column, "s" means slow, "m" means moderate and "f" means fast. In Run No. 4 the ratio of $Ru_3(CO)_{12}$ to $H_2O$ was 1:22. In Run No. 18, 200 mg of 5% Pt/C were used and in Run No. 20, 150 mg of 5% Pd/C were used with 4.15 grams of octamethylcyclotetrasilazane.

EXAMPLE 17

Reaction of Hexamethylcyclotrisilazane with Ammonia and Hydrogen

A reactor loaded with hexamethylcyclotrisilazane, (4.4 g) and $Ru_3(CO)_{12}$ (16 mg) was pressurized with $NH_3$(150 psi) and $H_2$(150 psi), then heated at 135° C. for 18 hours. The cyclotrimer was converted in 84% yield to form two major series of products: cyclomers (A; n=4–13) and branched cyclomers (B; n=1–6) analyzed by GC-MS.

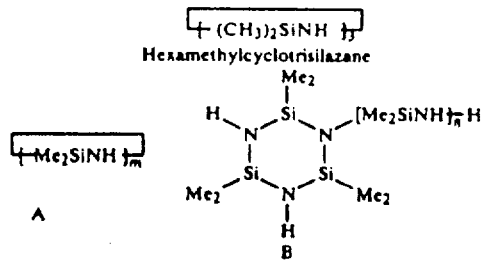

EXAMPLE 18

Copolymerization of Phenylsilane and 1,1,3,3-Tetramethyldisilazane

To a mixture of phenylsilane (4.32 g, 40 mmole) and 1,1,3,3-tetramethyldisilazane (5.32 g, 40 mmole) was added $Ru_3(CO)_{12}$ (16 mg, 25 μmol). The solution was heated at 60° C. under 150 psi of ammonia. After 5 h, the GC shows high boiling products and the loss of 95% of the starting materials. After 8 hours, the reaction temperature was increased to 90° C. and after another 2 hours to 135° C. The reaction was run for 30 hours. The final result was a viscous oil consisting of a mixture of products. Very little material came off the GC at this point which was indicative of high molecular weight products. Evaporation of the remaining volatile products (230° C./2 mm) leaves a waxy residue. IR, NMR and GC/MS of this product were taken to examine the copolymerization between the two starting substrates. An Si—H bond appears clearly in the IR spectrum (although it is not observed in the NMR spectrum which was analytically less sensitive). The elemental analysis and the NMR integration suggest that the copolymer contains the following average structure.

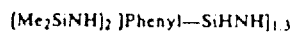

This copolymer is believed to be a new composition of matter.

| Elemental analysis: | C | H | N | Si |
|---|---|---|---|---|
| Calculated for suggested structure: | 46.69 | 7.61 | 15.23 | 30.44 |
| Found | 46.45 | 7.05 | 15.91 | 30.88 |

EXAMPLE 19

Reaction Between Hexamethylcyclotrisilazane and Diethylsilane 15 mg (25 μmol) of $Ru_3(CO)_{12}$ were added to 2.19 g (10 mmol) of hexamethylcyclotrisilane ($+Me_2SiNH_{\frac{1}{3}}$) and 0.88 g (10 mmole) of diethylsilane ($Et_2SiH_2$). The solution was heated at 135° C. for 20 h. N-diethylsilane-hexamethylcyclotrisilazane

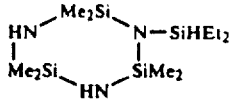

was the major product (3.7 mmole/ identified by GC-MS and NMR. Other minor products were ($HEt_2$-$Si)_2NH$ and bis-(N-diethylsilyl)-hexamethylcyclotrisilazane. A residue of 28% yield remained after evaporation at 180° C. (0.5 mm). The (N-diethylsilyl)-cyclotrisilazane, believed to be a new composition of matter, was isolated by distillation and identified by GC-MS and NMR.

EXAMPLE 20

Reaction of 1,2,3,4,5,6-Hexamethylcyclotrisilazane with Ammonia

To 4.39 g of [MeSiH—NMe]₃ were added 16 mg of $Ru_3(CO)_{12}$. The solution was heated under 150 psi of ammonia at 60° C. The reactant disappeared after 5 hours. The reactor was again charged with ammonia and heated at 90° C. for 33 hours. The product was a viscous oil having $\overline{Mn}=691$ which gave a 57% yield of ceramic material. GC-MS analysis of the oligomeric fraction indicated the substitution of Si—H groups by Si—NH groups together with the substitution of N—Me groups by N—H in the cyclomeric structure. The product is believed to be a new composition of matter.

EXAMPLE 21

Polymerization of Tetramethyldisilazane in the presence of Ammonia (a) To 100.0 mmole of TMDS (13.3 g) were added 50.0 μmol of $Ru_3(CO)_{12}$ (32.0 mg) and the solution was heated under ammonia under various reaction conditions as noted in Table 10. The volatile oligomers were separated from the solution by vacuum distillation (up to 180° C./300μ). The residue was the nonvolatile fraction.

Our initial evaluation of this reaction, using either the homogeneous ruthenium catalyst or activated Pt/C gave cyclomers (n=3-7), linear oligomers (n=2-11), and very small amounts of branched oligomers, (n=1-7; <5%) as evidenced by the GC-MS analyses.

additives and the formation of increased amount of latent reactive groups providing thermosetting properties to the polymers.

EXAMPLE 23

Catalytic Formation of Extended Polymers

To 50 g N-methylsilazane $CH_3NH$—$(H_2SiNCH_3)_x$—H ($\overline{Mn}$=1050) were added 100 mg $Ru_3(CO)_{12}$ and the mixture was heated at 90° C. Samples were taken out of the solution and measured by GPC (Gel Permeation Chromatography), VPO and Rheometry instruments. The results are shown in Table 12 and plotted in FIG. 1. All samples, including starting material, show a very broad distribution. The higher molecular weight limit (for observable species) was increased from 50,200 D in the starting materials to 1,000,000 to 2,000,000 after 100 hours. Two new maximum peaks are built up around 28,000 and 55,000 D. Although increases in $\overline{Mn}$ were not observable after 40 hours, the higher molecular weight fraction continues to grow as indicated by the high $\overline{Mw}$ and $\overline{Mz}$ values, determined by GPC. These results are evidence of the extremely high

TABLE 10

The Effects of Temperature and Ammonia Pressure on Product Selectivity in the Reaction Between TMDS and $NH_3$ in the Presence of $Ru_3(CO)_{12}$

| Run | NH | Temp. (°C.) | Time[a] (Hours) | Turnover[b] Frequency | | Yield of Cyclomers in the Volatile Fraction (%) | | Nonvolatile Oligomer Yield (%) | Ave. M.W. ($\overline{Mn}$) |
|---|---|---|---|---|---|---|---|---|---|
| | | | | TMDS Conversion | Si—H Disappearance | Total | Tricyclomer | | |
| 1 | 1 | 60 | 66 | 640 | 1000 | 39 | 25 | 19 | 1297 |
| 2 | 1 | 90 | 60 | 720 | 1160 | 34 | 18 | 21 | 1006 |
| 3 | 13 | 60 | 12 | 1220 | 1300 | 88 | 69 | 19 | 2024 |
| 4 | 13 | 90 | 8 | 1960 | 3438 | 91 | 70 | 5 | 1425 |

[a]At these reaction time periods, the catalyst was still active but the rate of reaction was considerably reduced because of the low Si—H bond concentration.
[b]TF (mol substrate/mol cat/h) based on initial rates, determined by GC (TMDS conversion) and NMR integration (Si—H signal disappearance) referred to the $CH_3$—Si signals.

EXAMPLE 22

Catalytic Formation of Extended Polymers

An N-methylpolysilazane, $CH_3NH$—$(H_2SiNCH_3)_x$—H ($\overline{Mn}$=1100) was reacted with $Ru_3(CO)_{12}$ under different conditions (e.g., reaction time and temperature, ammonia and monomethylamine environment). Samples were taken out of the reactions solutions; solvents were evaporated and $\overline{Mn}$ measurements were performed on VPO equipment. The results are shown in Table 11.

TABLE 11

| Run | Amounts | | | Gas Phase | Temperature (°C.) | Time (h) | $\overline{Mn}$ (daltons) |
|---|---|---|---|---|---|---|---|
| | Polymer (g) | Catalyst (mg) | THF (ml) | | | | |
| 1 | 1.0 | 4.0 | 5.0 | $N_2$ | 60 | 10 | 1420 |
| 2 | 2.0 | 4.0 | 5.0 | $N_2$ | 60 | 20 | 1230 |
| 3 | 6.0 | 12.0 | — | $N_2$ | 90 | 20 | 1620 |
| 4 | 6.0 | 24.0 | 12.0 | $N_2$ | 60 | 10 | 1550 |
| 5 | 6.0 | 24.0 | 12.0 | $N_2$ | 90 | 10 | 1380 |
| 6 | 6.0 | 12.0 | 12.0 | $N_2$ | 60 | 10 | 1300 |
| 7 | 4.0 | 16.0 | 8.0 | $NH_3$ | 60 | 10 | Gel |
| 8 | 4.0 | 16.0 | 8.0 | $CH_3NH_2$ | 60 | 10 | Gel |

The polymers obtained in runs 7 and 8 were soluble in the reaction solution and cross-linked upon solvent evaporation. Therefore, they are excellent candidates for binder and coating applications. Runs 7 and 8 prove the reactivity of the SiH polymers toward N—H bond polymers which are obtained by the direct ammonolysis and by the catalytic activation, chain extension and cross-linking. Such tractable high molecular weight products were never reported in the current literature. Separation of the high molecular weight fraction(s) may be effected by either size exclusion chromatography, membrane or ultrafiltration, ultracentrifugation, or solvent/solvent fractionation from solutions or high vacuum distillation. The polymer viscosity increased dramatically during the reaction, starting at ~1.0 poise and ending at ~400-4500 poise. All samples except the 100 hour one behave in a newtonian fashion. The 100 hour sample shows a non-Newtonian viscosity between 4780 poise at a shear rate of 1.0 sec$^{-1}$ to 400 poise at a shear rate of 10.0 sec$^{-1}$.

TABLE 12

| Time (hours) | 1st Max.[b] (MW) | 2nd Max.[b] (MW) | 3rd Max.[b] (MW) | Highest (MW)[b] | $\overline{Mn}^c$ (GPC) | $\overline{Mw}^c$ (GPC) | $\overline{Mz}^c$ (GPC) | $\overline{Mn}^d$ (VPO) | D[e] | Viscosity (poise)[f,i] |
|---|---|---|---|---|---|---|---|---|---|---|
| 0 | 2.1K | — | — | 50K | 1,100 | 3,970 | 13,080 | 1050 | 3.6 | 5 |
| 10 | 2.6K | 23K | — | 120K | 2,040 | 10,450 | 38,220 | 1290 | 5.1 | — |
| 20 | 2.6K | 23K | 50K | 160K | 2,130 | 12,660 | 47,010 | 1390 | 5.9 | — |
| 30 | 2.6K | 28K | 50K | 320K | 2,140 | 17,990 | 86,840 | 1430 | 8.4 | 18 |
| 40 | 2.6K | 32K | 55K | 230K | 2,280 | 19,510 | 78,430 | 1530 | 8.5 | 55 |
| 50 | 2.6K | 35K | 55K | 320K | 2,570 | 20,990 | 86,710 | 1710 | 8.2 | 58 |
| 65 | 2.6K | 32K | 60K | 520K | 2,320[h] | 23,620 | 127,620 | 1760 | 10.6 | 98 |
| 100[i] | 2.6K | 33K | 320K | 2,480K | 2,060[h] | 46,290 | 553,020 | — | 23.0 | 4,800 |

[a]GPC equipped with 4 size exclusion columns suitable for separation between 100 and 1,000,000 D. THF was used as a solvent and polystyrene standardization curve.
[b]Maxima of the GPC distribution curve and highest molecular weight species observed by GPC.
[c]Molecular weight determined by GPC.
[d]Measured by VPO techniques.
[e]D = dispersion of polymer; D = Mw/Mn.
[f]Measured by rheometer at 30° C.
[g]Difficulties were found in filtration; true values may be higher.
[h]Lower Mn may suggest branching or cross-linking of the polymer.
[i]The polymer behaves in a non-Newtonian fashion. For a shear rate of 1.0 sec$^{-1}$, the viscosity value was 4,800 poise. For a shear rate of 10 sec$^{-1}$, the viscosity value is 400 poise.

EXAMPLE 24

Reactions of Methylsiloxanes with Dimethylamine a. 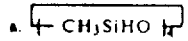

To 6.0 g (100 mmole)

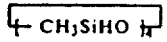

were added 32 g (0.05 mmole) of Ru$_3$(CO)$_{12}$. The solution was charged with approximately 100 psi of dimethylamine. The reaction was carried out at 60° C. and detected by the observed pressure formed in the reactor. The pressure was released every 0.5-1 hour and the reactor was recharged with fresh dimethylamine. After 6 hours, a total pressure of 1100 psi dimethylamine was charged into the reactor yielding a total pressure of 770 psi. No more gas evolution was observed. 8.1 g of viscous oily products were obtained, indicating 49% yield of amino substitution. This yield is correlated with the $^1$H—NMR analysis of the solution showing 53% of amine substitution and 29% of Si—H groups. GC-MS analysis shows that bis and tris substituted cyclotetramers were the major products when mono and tetrakis appear only in small quantities. The $\overline{Mn}$ of the product was 604 D. Elemental analysis: Si(25.33); N(12.59); C(30.71); H(8.15); O(19.87). Pyrolysis under N$_2$ gave a ceramic yield of 14% and under NH$_3$ a ceramic yield of 61%.

b. [CH$_3$SiHO]$_{29}$

The reaction was run with the same quantities of starting materials and under the same conditions as the tetramer reaction of (a). Only 50 psi of dimethylamine was charged into the reactor each time. A total pressure of 500 psi dimethylamine was charged and 375 psi of hydrogen were evolved after 6 hours. 7.4 g of a very viscous polymer was obtained (33% yield of amino substitution) which was correlated to the $^1$H—NMR analysis showing similar results (36% of amine substitution and 45% of Si—H referred to the Si—CH$_3$ group). The $\overline{Mn}$ of the product was 1976.0 D. Elemental Analysis: Si(28.89); N(7.77); C(28.68); H(7.51); O(20.85). Pyrolysis under N$_2$ and NH$_3$ gave ceramic yields of 25% and 70%, respectively.

EXAMPLE 25

Reaction of Silane with Ammonia

To a stainless steel reactor containing a solution of 32 mg Ru$_3$(CO)$_{12}$ in 10 ml THF were charged 40 psi of SiH$_4$ and 60 psi of NH$_3$. The reactor was heated for 6 hours at 60° C. IR analysis indicates the formation of silazanes. A insoluble solid material (300 mg) obtained after solvent removal was characterized as intractable silazane resin. Elemental analysis of this product shows THF or THF products trapped in the solid material. This analysis fits the molecular structure of [(NH)$_{0.5}$SiHNH]$_x$ after calculated corrections for the presence of THF products and catalyst. Pyrolysis of the solid gave an 86% ceramic yield.

IR Analysis:

Solvent IR (THF), ref THF, cm$^{-1}$:NH$_2$ 3380–3320; NH 3280; Si—H 2157, 2142, 880; Si—NH$_2$ 1155; Si—NH—Si 1150, 972.

Solid IR (KBr, cm$^{-1}$): NH$_2$, NH 3700–3000; Si—H 2166, 885; Si—NH—Si 1150, 1045, 960, (all very broad

| Elemental Analysis of Polymer Product (%): | | | | | |
|---|---|---|---|---|---|
| Si | N | H | C | O | Ru |
| 36.25 | 14.10 | 4.68 | 12.11 | 23.06 | 9.08 |

Such a reaction may also be used in the preparation of ceramic products.

EXAMPLE 26

Reaction of Silane with Methylamine

To a stainless steel reactor containing a solution of 16 mg Ru$_3$(CO)$_{12}$ in 10 ml THF were charged 60 psi SiH$_4$ and 60 psi MeNH$_2$. The reactor was heated at 60° C. for 4 hours. A pressure of 120 psi was built up during the reaction period. The solution was homogeneous and 380 mg of oily products remained after solvent removal. This oil became more viscous as a result of cross-linking at room temperature under inert atmosphere. Several $^1$H—NMR singlets of Si—H as well as 2 N—CH$_3$ singlets suggest different types of silazane bonds. Indeed, GC-MS analysis provides evidence to the formation of cyclosilazanes containing aminic and silylaminic side groups. $^1$H—NMR: Si—H 4.62, 4.49, 4.38 (7H); N—CH$_3$ 2.52, 2.48 (3OH).

EXAMPLE 27

Synthesis of Et$_3$SiNH$_2$

To 20 mmole (3.2 ml) Et$_3$SiH were added 0.05 mmole (11 mg) Pd(OAc)$_2$ and the solution was heated at 100° C. under N$_2$ for 5 minutes to reduce Pd$^{II}$ to Pd°. The solution was cooled to 21° C. and then dry ammonia was bubbled through the solution to complete the silane transformation to silylamine in 4 hours. Completion of the reaction was observed by gas chromatography as well as by tapering off of the vigorous hydrogen evolution which occurred during the reaction. The reaction mixture was filtered under N$_2$ and distilled under N$_2$ (138° C.) to provide analytically pure silylamine with yields higher than about 90%.

EXAMPLE 28

Reaction of Et$_3$SiNH$_2$ with Et$_3$SiH

To a solution of 9 mmole (2 ml) Et$_3$SiNH$_2$ in 5 ml THF were added 16 mg of Ru$_3$(CO)$_{12}$ and 9 mmole of Et$_3$SiH. The reaction was completed after 20 min at 70° C. and product formation (over 95% yield) was followed by GC.

EXAMPLE 29

Reactions of Oligo- and Polymethylsiloxane With Ammonia a. 0.05 mmole (32 mg) Ru$_3$(CO)$_{12}$ was added to 100 mmole (6.0 g)

and the solution was heated at 60° C. under 200 psi of ammonia. Gas evolution formed a pressure of 400 psi in 19 hours and hard rubber was formed. The product's elemental analysis showed the presence of 5.55 Wt % which indicated a nitrogen-silicon ratio of 0.28 (Table 13). Oxygen content was in a ratio of 1.29 per silicon. Some of the oxygen excess was a result of oxygen contamination found in the commercial starting material and detected by NMR intensity ratio of Si—H/Si—CH$_3$ absorbance (0.8:1.0). The product was pyrolyzed at 850° C. both under nitrogen and ammonia atmosphere. Elemental analysis of the pyrolyzed material suggested a mixture of the following ceramic components (mol ratio): SiO$_2$(0.62); Si$_3$N$_4$(0.23); SiC(0.14); C(0.58). Pyrolysis under a slow stream of ammonia reduced almost totally, the carbon content as well a some of the oxygen excess and increased significantly the nitrogen content.

Very similar results were observed when the cyclotetramer was replaced by polymethylsiloxane having a number average molecular weight ($\overline{Mn}$) of 1880 (degree of polymerization was 29) as shown in Tables 13 and 14. The comparison between cyclo and polysiloxane reactions revealed that less nitrogen interacted with the polymer than with the cyclomer and the SiC fraction in the product pyrolyzed under nitrogen was higher for the polymer reaction. However, no real difference was shown when both were pyrolyzed under ammonia. The pyrolysis was not completed as there was an excess of oxygen (assuming that Si$_2$ON$_2$ was the major product and that the silicon excess forms SiO$_2$).

The ceramic yields were very high for all types of reactions and pyrolysis procedures.

b. A solution of 100 mmole (6.0 g) of

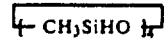

and 25.0 μmol (8 mg) Ru$_3$(CO)$_{12}$ was heated at 60° C. under 100 psi of ammonia. After 2 hours 220 psi of pressure were formed and the product was obtained as a viscous liquid having $\overline{Mn}=1230$ D. The pressure was released and recharged with an additional 100 psi of ammonia. 200 psi of gas were evolved in a 2-hour period and the viscous liquid was converted to a soft rubber.

$^1$H NMR integration revealed that 41% of Si—H bonds were replaced by ammonia to form Si—NH$_2$ and Si—NH— bonds. Elemental analysis showed that the incorporation ratio of 0.24 nitrogen per carbon, which indicated the formation of cyclosilazane chain polymer bridged by ammonia. A dimer of two cyclotetramers bridged by a single —NH was the major product found by GC-MS analysis.

IR of CCl$_4$ solutions shows new sharp stretches at 3420 (w), 3380 (m) cm$^{-1}$ together with new shoulders at 1240 and 1160 cm$^{-1}$.

$^1$H NMR (CDCl$_3$ δ, Ref CHCl$_3$): Si—H (4.69, 0.59H), NH (1.10, 0.16H) CH$_3$ (0.22, 3H).

| Elemental Analysis: | C | H | N | Si |
|---|---|---|---|---|
| Found (%) | 19.94 | 6.14 | 5.39 | 42.23 |
| mol ratio | 1.00 | 3.70 | 0.24 | 0.91 |

TABLE 13

The Elemental Analysis of Polymers and Ceramics Obtained in a Catalyzed Reaction Between Methylsiloxanes and Ammonia

| Product | Analysis % (mole ratio) | | | | |
|---|---|---|---|---|---|
|  | Si | O | N | C | H |
| Cyclotetramer Reaction | | | | | |
| Polymer | 40.70 | 29.85 | 5.55 | 18.02 | 5.88 |
|  | (1.00) | (1.29) | (0.28) | (1.03) | (4.06) |
| Ceramic material under N$_2$ | 45.73 | 32.53 | 6.94 | 14.10 | 0.79 |
|  | (1.00) | (1.25) | (0.31) | (0.72) | (0.48) |
| Ceramic material under NH$_3$ | 47.76 | 28.26 | 21.81 | 1.35 | 0.57 |
|  | (1.00) | (1.04) | (0.91) | (0.06) | (0.33) |
| Polymer Reaction | | | | | |
| Polymer | 42.47 | 27.80 | 4.06 | 19.67 | 6.00 |
|  | (1.00) | (1.14) | (0.19) | (1.07) | (3.95) |
| Ceramic material under N$_2$ | 48.12 | 32.81 | 5.02 | 13.65 | 0.76 |
|  | (1.00) | (1.19) | (0.21) | (0.66) | (0.44) |
| Ceramic material under NH$_3$ | 48.29 | 28.35 | 21.01 | 1.75 | 0.54 |
|  | (1.00) | (1.03) | (0.87) | (0.09) | (0.31) |

TABLE 14

Ceramic Yield of the Pyrolyzed Polymers Obtained in a Catalytic Reaction Between Methylsiloxanes and Ammonia

| Reactant | Pyrolysis Conditions | Ceramic Yield (%) |
|---|---|---|
| Cyclotetramer | N$_2$ | 77 |
| Cyclotetramer | NH$_3$ | 84 |
| Polymer | N$_2$ | 75 |
| Polymer | NH$_3$ | 88 |

EXAMPLE 30

Kinetic Studies

In a typical kinetic reaction, a small quantity of the solid catalyst was carefully weighed and placed in a glass reactor. The reactor was then capped with a septum sealed head and the system was purged with argon for at least 15 minutes. Freshly dried THF, followed by 3.14 mmole of triethylsilane, 0.513 mmole of n-decane and 2.38 mmole of n-butyl amine were introduced into the reactor via syringe. The solution mixture was then placed in an oil bath at 70° C. for reaction. Aliquots were drawn out at timed intervals for GC analyses. In cases where reaction did not occur at 70° C., the temperature was raised to 100° C.

TABLE 15

| Initial Reaction Rate of Catalytic Reaction Between Et$_3$SiH and n-BuNH$_2$ | |
|---|---|
| Catalyst | Initial Reaction Rate Relative to Ru$_3$(CO)$_{12}$ |
| Ir$_4$(CO)$_{12}$ | 0.25$^a$ |
| Os$_3$(CO)$_{12}$ | 0.30$^b$ |
| H$_2$Os$_3$(CO)$_{10}$ | 0.45$^b$ |
| Rh$_6$(CO)$_{16}$ | 0.17$^a$ |
| Ru$_3$(CO)$_{12}$ | 1.00$^a$ |
| H$_4$Ru$_4$(CO)$_{12}$ | 0.03$^a$ |
| PdCl$_2$ | 13.3$^a$ |
| Pd/C | 5.62$^a$ |
| Pd(OAc)$_2$ | 12.8$^a$ |
| ($\phi$CN)$_2$PdCl$_2$ | 16.9$^a$ |
| Pt/C | 0.18$^a$ |

$^a$Bath temperature 70° C.
$^b$Bath temperature 100° C.

EXAMPLE 31

Gradual Pyrolysis of Silazanes

For polysilazane polymers based on n-methyl polysilazane, CH$_3$NH—(H$_2$SiNCH$_3$)$_x$—H with average x>10, that were reacted with Ru$_3$(CO)$_{12}$ catalyst and other components, e.g., MeHN$_2$, Me$_2$NH, and NH$_3$, we have determined that the yield for conversion to ceramic material when heated in N$_2$ atmospheres were strongly dependent on heating rate. Polymers heated in N$_2$ at 0.5° C./min gave yields between 67-70 wt % (ceramic material) while polymers heated at 5° C./min gave yields of under 60%. The maximum temperature for these pyrolyses reactions was ~800° C. It has also been found that isothermal holds during pyrolysis at ~110° C. for 3 hours additionally increased the ceramic yields by up to 6 wt %. Yield differentials with respect to heating rate variations can be correlated with differences in weight loss versus temperature between 300°-500° C. While not wishing to be bound by any particular theory, it is postulated that yield differentials with respect to the presence or absence of isothermal curing steps during pyrolysis may be due to latent reactivity of Si—H bonds and the presence of small amounts of catalyst in the polymer.

EXAMPLE 32

TGA Pyrolysis

Figure 2:
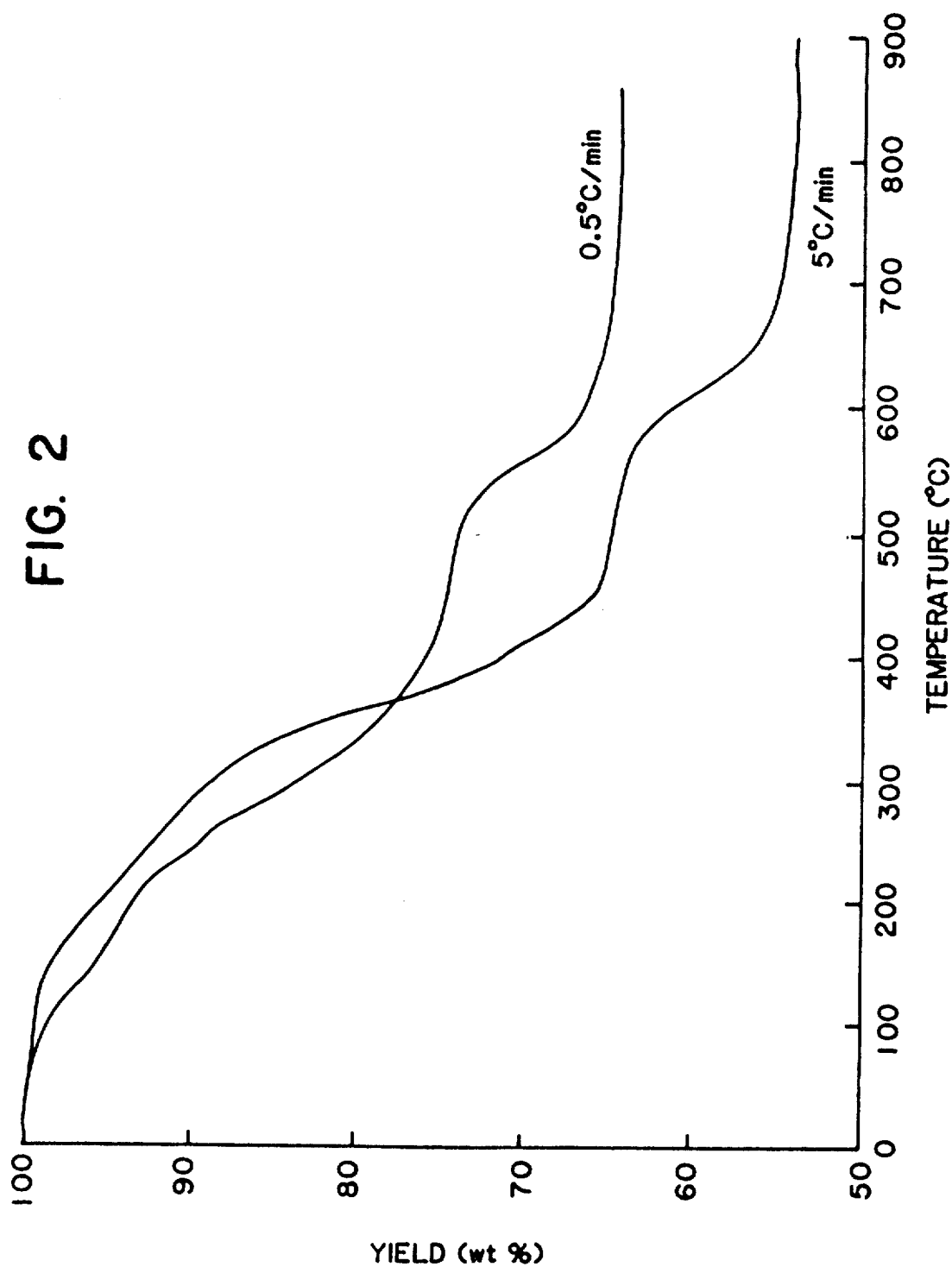
FIG. 2 graphically represents TGA pyrolysis of a polysilazane at different temperature ramping rates.

To 10 g of CH$_3$NH—(H$_2$SiNCH$_3$)$_x$—H prepared as in Example 2 were added 20 mg of Ru$_3$(CO)$_{12}$ and the solution was heated at 90° C. for 8 h. The viscous polymer obtained in the reaction was then pyrolyzed in TGA equipment at temperature ramping rates of 5.0° C./min and 0.5° C. per minute. FIG. 2 shows the dependence of the ceramic yield on the heating rate. The weight lost between 200° C. and 400° C. was retarded by about 10% in the slow pyrolysis due to the increase in thermal cross-linking reactions and the decrease in volatilization of compounds. At this temperature range, the products evaporated out of the resin material were mostly low molecular weight silazane oligomers. Below 200° C., the weight lost was primarily due to hydrogen and methylamine release, suggesting that control of the temperature within this range increases the amount of cross-linking in the pyrolyzed material.

EXAMPLE 32

Pyrolysis Under N$_2$ or NH$_3$

Various polymers containing [H$_2$SiNCH$_3$] monomeric units were pyrolyzed under N$_2$ and ammonia at different temperature ramping rates (see Table 16). Table 16 indicates the following: (1) slow pyrolysis rates increase the ceramic yields; (2) low temperature holds during the pyrolysis schedule slightly increase the ceramic yields; (3) higher molecular weights give in general higher ceramic yields; (4) extended polymers produced by catalytic activity give higher ceramic yields; and (5) polymers treated with catalyst in the presence of ammonia give higher ceramic yields than in the absence of ammonia.

Table 17 shows the elemental analysis of pyrolyzed polymers from different runs set forth in Table 16. As may be seen in Table 17, the carbon content of ceramics derived from polymer reacted with catalyst in an ammonia or gaseous amine atmosphere was significantly lower than polymer reacted under nitrogen. Pyrolysis under ammonia or other amine thus substantially reduces the carbon content of the ceramic product.

TABLE 16

| | | Pyrolysis of [H$_2$S:NCH$_3$]$_x$-based Polymers | | | | | | | |
|---|---|---|---|---|---|---|---|---|---|
| | Polymer Type | Reaction Conditions | | | | Pyrolysis Conditions | | | |
| Run | Mn; synthesis; polymer: catalyst wt ratio: | Temp (°C.) | Time (hours) | Gas Phase (psi) | Product Phase | Heating °C./min | Gas phase | Holds (°C; hrs) | Ceramic Yield (900° C.) |
| 1 | $^a$Mn = 323; direct aminolosis at 0° C. | — | — | — | nonvisc liq | 5.0 | N$_2$ | — | 28 |
| 2 | $^a$Mn = 566; nonvolatile fraction of 1. | — | — | — | nonvisc liq | 5.0 | N$_2$ | — | 38 |
| 3 | Mn = 800; direct aminolosis at −78° C.; without volatiles distillation. | — | — | — | visc liq | 0.5 | N$_2$ | — | 45 |
| 4 | Mn = 1100; as in 3. | — | — | — | visc liq | 0.5 | N$_2$ | — | 49 |
| 5 | Mn = 1770; as in 3 with 10% HSiCl$_3$ | — | — | — | visc liq | 0.5 | N$_2$ | — | 45 |
| 6 | Mn = 1490; with Ru$_3$(CO)$_{12}$: 500; starting Mn = 1150 | 90 | 8 | N$_2$ | visc liq | 5.0 | N$_2$ | — | 54 |
| 7 | As in 6 | 90 | 8 | N$_2$ | visc liq | 0.5 | N$_2$ | — | 64 |

TABLE 16-continued

Pyrolysis of [H$_2$S:NCH$_3$]$_x$-based Polymers

| | Polymer Type | Reaction Conditions | | | | Pyrolysis Conditions | | | |
|---|---|---|---|---|---|---|---|---|---|
| Run | Mn; synthesis; polymer: catalyst wt ratio: | Temp (°C.) | Time (hours) | Gas Phase (psi) | Product Phase | Heating °C./min | Gas phase | Holds (°C; hrs) | Ceramic Yield (900° C.) |
| 8 | As in 6 | 90 | 8 | N$_2$ | visc liq | 0.5 | N$_2$ | 130:24 | 66 |
| 9 | As in 6 | 90 | 8 | N$_2$ | visc liq | 0.5 | N$_2$ | 200:24 | 68 |
| 10 | Mn = 1600; as in 9 | 90 | 20 | N$_2$ | vy visc liq | 0.5 | N$_2$ | | 67 |
| 11 | $^b$Mn > 1800; as in 10 | 90 | 26 | CH$_3$HN$_2$ | visc liq (wax) | 0.5 | N$_2$ | | 69 |
| 12 | As in 11 | 90 | 26 | CH$_3$NH$_2$ | visc liq (wax) | 5.0 | N$_2$ | | 57 |
| 13 | $^c$gel; with Ru$_3$(CO)$_{12}$: in THF; 250 | 60 | 10 | NH$_3$ | soft rubber | 0.5 | N$_2$ | — | 77 |
| 14 | As in 13 | 60 | 20 | NH$_3$ | soft rubber | 0.5 | N$_2$ | — | 83 |
| 15 | As in 4 | — | — | — | visc liq | 0.5 | NH$_3$ | — | 49 |
| 16 | As in 6 | 90 | 8 | N$_2$ | visc liq | 0.5 | NH$_3$ | — | 65 |

*Reported by Seyferth et al.
$^b$Partially insoluble in toluene for VPO measurements.
$^c$Soluble in THF solution, cross-linked during solvent removal.

TABLE 17

Elemental Analysis

| Run (From Table 16) | Elemental Analysis (mole ratio) | | | | |
|---|---|---|---|---|---|
| | Si | N | C | H | O |
| 4 | 45.8 | 32.5 | 18.8 | 1.0 | 2.0 |
| 6 | 48.8 | 32.8 | 17.5 | 0.8 | 0.1 |
| 12 | 45.0 | 34.0 | 18.9 | 0.8 | 1.4 |
| 13 | 49.3 | 31.5 | 16.2 | 1.10 | 2.2 |
| 15 | 52.0 | 34.0 | 0.7 | 1.2 | 1.55 |
| 16 | 56.0 | 32.6 | 4.3 | 0.7 | 0.1 |

EXAMPLE 34

Silicon Oxynitride Ceramic

X-ray powder diffraction analyses of the ceramic products obtained by the procedure described in Example 29 show a clear spectral pattern of orthorhombic Si$_2$ON$_2$ when the polymeric products were pyrolyzed under NH$_3$ (pyrolysis under N$_2$ gave relatively poor crystallization under the same conditions). These patterns are found only when the total amorphous ceramic products produced at 900° C. are reheated to 1600° C. under N$_2$. No other types of ceramic crystallites were observed in the X-ray powder diffraction spectra. Less than 0.45 wt. % carbon was found, and the silicon content of the product was 51–56 wt. % (theoretical: 56 wt. %), suggesting substantially pure silicon oxynitride in the ceramic mixture.

EXAMPLE 35

Fabrication of Ceramic Articles Using Silicon Nitride as a Binder

This example illustrates a process for the fabrication of ceramic bodies from a mixture of preceramic polysilazane and ceramic powders. The silicon and nitrogen containing polymers as prepared in the previous Examples display controllable chemical, mechanical, rheological, and pyrolytic properties that make them suitable as binders or forming aids. When mixed with ceramic powders such as Si$_3$N$_4$, the polymer/powder system can be compression molded into a variety of shapes. Pyrolytic release of the organic components bound to the polysilazane above 800° C. provided an amorphous Si$_3$N$_4$ material that partially fills the pore system that exists in powder compacts. This partial filling decreases the porosity of the body and increases its green density, which is advantageous for subsequent sintering steps at temperatures in excess of 1700° C.

The preceramic polymer used in this process was a polysilazane having the approximate structure (H$_2$SiNCH$_3$)$_x$. This polysilazane was synthesized by the procedure described in U.S. Pat. No. 4,612,383, cited supra. This method allows for control of the degree of polymerization and the viscosity of the polysilazane, an important characteristic for any binder material. In a typical experiment, (H$_2$SiNCH$_3$)$_x$ ($\overline{M}_n$ = 1265 D; viscosity ~ 1 poise) was heated at 90° C. for 55 h with Ru$_3$(CO)$_{12}$ as catalyst. It was then dissolved in THF and filtered. The solvent was removed by vacuum evaporation (P$_{Hg}$ ~ 1 mm). The resulting polymer ($\overline{M}_n$ = 1420 D; viscosity ~ 50 poise; density = 1.03 g/cm$^3$) was redissolved in THF to form a standard solution of 0.059 g/ml. A powder such as Si$_3$N$_4$ was added to the standard solution in different mixing ratios and dispersed ultrasonically. THF was again removed by vacuum evacuation, leaving a homogeneous polymer/powder mixture. The mixture was loaded into a steel die and under an inert atmosphere of N$_2$ and compression molded at pressures of 5000 to 45,000 psi. The die was coated with tetramethyldisilazane or hexamethyldisilazane as a mold release. The formed body, already a rigid article hard enough to be displaced without any significant precautionary measures (other than reduction of exposure to moisture), was then heated to ~ 800° C. in N$_2$ at 0.5°–5° C./min to convert the polymer to ceramic material. The pyrolyzed bodies have densities up to 2.9 g/cc, indicating porosities of less than 15% for unsintered pieces. Sintering of the body to final density occurs at 1725° C. in an overpressure of N$_2$.

By contrast, polymer/powder mixtures were also processed by mechanical mixing of liquid polysilazanes with ceramic powder. This variation of the above procedure resulted in inferior formed bodies caused by insufficient homogeneity of the polymer/powder mixture due to inadequate mixing. The consequence of this was an unsatisfactory distribution of polymer with respect to the ceramic powder. The sintered bodies fabricated by this method had final densities of 2.7 g/cc or less. This demonstrates the efficacy of solution mixing of polymer and powder to achieve homogeneity. Using a stock solution of polymer also simplifies handling of these oxygen- and water-sensitive polymers.

A range of polymer/powder ratios have been examined from 10–30 wt % polymer. Polymer/powder ratio can have a crucial effect on the green density of the pyrolyzed body and the degree of damage during pyrolysis. The optimum ratio of 15–20 wt % polymer ensures the maximum green density with enough porosity in the pressed body to ensure that volatile components of the polymer can be removed during pyrolysis without damage to the body.

EXAMPLE 36

Preparation of Ceramic Bodies from Preceramic polysilazane and Ceramic Powders

A polysilazane $CH_3NH-(H_2SiNCH_3)_x-H$ as prepared in Example 2 ($\overline{M}_n = 1100$ D; viscosity ~ 1 poise) was heated at 90° C. for 55 h with $Ru_3(CO)_{12}$ as catalyst. It was then dissolved in THF and filtered. The solvent was removed by vacuum evaporation ($P_{Hg} \sim 1$ mm). The resulting polymer ($\overline{M}_n = 1420$ D; viscosity ~ 50 poise; density = 1.03 g/cm$^3$) was redissolved in THF to form a standard solution of 0.059 g/ml. A ceramic powder consisting of 79.81 wt. % $Si_3N_4$, 11.37 wt. % $Y_2O_3$, 5.69 wt. % $Al_2O_3$, and 3.13 wt. % $SiO_2$ was mixed in a ball mill for 24 h with $Si_3N_4$ balls and methanol. After evaporation of the methanol, 8.002 g of powder were added to 33.90 ml of polymer solution and dispersed ultrasonically. The THF was removed by vacuum evacuation, leaving a homogeneous powder/polymer that was 80 wt. % ceramic powder and 20 wt. % polymer. The mixture was loaded in a steel die under $N_2$ and compression molded at 27,000 psi. The die was coated with tetramethyldisilazane as a mold release. The formed body was heated under 1 atm $N_2$ at 0.5° C./min to 800° C. to convert the polymer to ceramic material. The volume of pores in this pre-sintered piece was 0.114 cm$^3$/g. which corresponds to a green density of 75%. The piece was then sintered at 1725° C. at 8 atm of $N_2$ for 6 h. After sintering, the piece was over 95% of theoretical density with no open porosity.

EXAMPLE 37

Preparation of Ceramic Bodies

A polysilazane solution and a ceramic powder composition were prepared as in the previous Example. The ceramic powders were mixed with $Si_3N_4$ and methanol as in the previous Example, and the methanol was evaporated. 10.20 g of powder were added to 30.40 ml of polymer solution and dispersed ultrasonically. The THF was removed by vacuum evacuation, leaving a homogeneous powder/polymer that was 85 wt. % ceramic powder and 15 wt. % polymer. The mixture was loaded in a steel die under $N_2$ and compression molded at 27,000 psi. The die was coated with hexamethyldisilazane as a mold release. The formed body was heated under 1 atm $N_2$ at 0.5° C./min to 800° C. to convert the polymer to ceramic material. The volume of pores in this pre-sintered piece was 0.15 cm$^3$/g, which corresponds to a green density of 68%. The piece was then sintered at 1725° C. at 8 atm of $N_2$ for 6 h. As in the previous Example, after sintering, the piece was over 95% of theoretical density with no open porosity.

EXAMPLE 38

Preparation of Ceramic Bodies

A polysilazane solution and a ceramic powder composition were prepared as in Example 35. The ceramic powders were mixed with $Si_3N_4$ and methanol as in Example 35, and the methanol was evaporated. 7.51 g of powder were added to 42.40 ml of polymer solution and dispersed ultrasonically. The THF was removed by vacuum evacuation, leaving a homogeneous powder/polymer that was 75 wt. % ceramic powder and 25 wt. % polymer. The mixture was loaded in a steel die under $N_2$ and compression molded at 45,000 psi. The die was coated with hexamethyldisilazane as a mold release. The formed body was heated under 1 atm $N_2$ at 0.5° C./min to 800° C. to convert the polymer to ceramic material. The volume of pores in this pre-sintered piece was 0.09 cm$^3$/g, which corresponds to a green density of 79%. The bodies showed damage after molding and pyrolysis due to excess polymer in the mixture which prevented an optimal powder/polymer ratio from being achieved. The volume fraction of the powder fell below 50%, indicating that the powder particles were not in contact in the molded body.

EXAMPLE 39

Preparation of Ceramic Bodies

A polysilazane solution and a ceramic powder composition were prepared as in Example 35. The ceramic powders were mixed with $Si_3N_4$ and methanol as in Example 35, and the methanol was evaporated. 7.51 g of powder were added to 42.40 ml of polymer solution and dispersed ultrasonically. The THF was removed by vacuum evacuation, leaving a homogeneous powder/polymer that was 75 wt. % ceramic powder and 25 wt. % polymer. The mixture was loaded in a steel die under $N_2$ and compression molded at 27,000 psi. The die was coated with tetramethyldisilazane as a mold release. The formed body was heated under 1 atm $N_2$ at 0.5° C./min to 800° C. to convert the polymer to ceramic material. The volume of pores in this pre-sintered piece was 0.06 cm$^3$/g, which corresponds to a green density of 85%. The bodies showed damage after molding and pyrolysis due to excess polymer in the mixture which prevented an optimal powder/polymer ratio from being achieved. The volume fraction of the powder fell below 50%, indicating that the powder particles were not in contact in the molded body.

EXAMPLE 40

Preparation of Ceramic Bodies

A polysilazane solution and a ceramic powder composition were prepared as in Example 35. The ceramic powders were mixed with $Si_3N_4$ and methanol as in Example 35, and the methanol was evaporated. 9.00 g of powder were added to 17.00 ml of polymer solution and dispersed ultrasonically. The THF was removed by vacuum evacuation, leaving a homogeneous powder/polymer that was 90 wt. % ceramic powder and 10 wt. % polymer. The mixture was loaded in a steel die under $N_2$ and compression molded at 27,000 psi. The die was coated with tetramethyldisilazane as a mold release. The formed body was heated under 1 atm $N_2$ at 0.5° C./min to 800° C. to convert the polymer to ceramic material. The volume of pores in this pre-sintered piece was 0.25 cm$^3$/g, which corresponds to a green density of 56%. The piece is then sintered at 1725° C. at 8 atm of $N_2$ for 6 h. As in the foregoing Examples, after sintering, the piece is over 95% of theoretical density with no open porosity.

EXAMPLE 41

Preparation of Ceramic Bodies

A polysilazane solution was prepared as in Example 35. To 30.4 ml of this solution were added 10.20 g of pure silicon nitride powder, and the suspension was dispersed ultrasonically. The THF was removed by vacuum evacuation, leaving a homogeneous powder/polymer that was 85 wt. % ceramic powder and 15 wt.

% polymer. The mixture was loaded in a steel die under N₂ and compression molded at 27,000 psi. The die was coated with hexamethyldisilazane as a mold release. The formed body was heated under 1 atm N₂ at 0.5° C./min to 800° C. to convert the polymer to ceramic material. The volume of pores in this pre-sintered piece was 0.106 cm³/g, which corresponds to a green density of 77%. Inspection of the microstructure of the piece with SEM analyses showed chemical or physical reaction between the polymer-derived material and the silicon nitride powder (see FIG. 3). This indicated the capability of using this system for solid state sintering of Si₃N₄ powder. Upon treatment to 1725° C. at 8 atm N₂, considerable grain growth occurred, although pore closure was not achieved (see FIG. 4). This is further evidence of solid state reactions occurring in a silicon nitride powder/polymer-derived glass system.

EXAMPLE 42

Preparation of Ceramic Bodies

A polymer solution was prepared as in Example 35, and mechanically mixed with a ceramic powder consisting of 79.81 wt. % Si₃N₄, 11.37 wt. % Y₂O₃, 5.69 wt. % Al₂O₃, and 3.13 wt. % SiO₂. The mixture contained 2.04 g of ceramic powder and 0.83 g of polymer for a mixture that was 71 wt. % powder and 29 wt. % polymer. The mixture was compression molded in a steel die at 15,000 psi using a hexamethyldisilazane mold release, and heated in vacuum at 150° C. while in the mold. The molded body was inferior in quality to that of the previous Examples because of insufficient homogeneity of the powder/polymer mixture, in turn due to inadequate mixing. The body was heated to 500° C. in N₂ at 2° C./min, held at 500° C. for 3 h, and then heated to 900° C. at 1° C./min. Cracks were seen in the body before and after pyrolysis. Upon sintering at 1725° C. for 6 h in 8 atm N₂, the body achieved only 80% of theoretical density.

EXAMPLE 43

Preparation of Ceramic Bodies

A polysilazane solution (CH₃NH[H₂SiNCH₃—$_x$H, $\overline{Mn}$ ~ 1100 D) was prepared substantially as in the previous Examples; in this Example, however, the polysilazane was not previously treated with catalyst. 8.502 g of ceramic powders (as set forth in Example 35) were mixed with 1.5 g polymer in a THF solution. The mixture was compression-molded in a steel die at 15,000 psi and pyrolyzed under N₂ as in the preceding Example. Upon the heating schedule described in the previous examples, a green density of about 72% was found.

EXAMPLE 44

Polysilazane Coatings

Coatings of polysilazane precursors were prepared by dipping flat, polished, stainless steel plates (1¼ × 1¼ × 1/16 inch) into polysilazane solutions (type CH₃NH—(H₂SiNCH₃)$_x$—H, $\overline{Mn}$ ~ 1400) in THF having concentrations of 5 wt. %, 10 wt. % and 20 wt. %. The samples were cured under the slow pyrolysis regime (heating rate of .00° C./hr) to a final temperature of 700° C. The cured coatings were shiny, transparent and smooth. Coatings on the stainless steel plates were brightly colored from the interference of reflected light. The thickness of the cured coating was estimated from the interference colors to be between 0.1 and 0.5 microns for the two dilute solutions and between 0.5 and 1.5 microns for the 20% solution. Light micrographs of the thin and the thick coatings showed that while thin coatings appeared quite uniform, thicker coatings displayed cracks and irregularities due to shrinkage during pyrolysis.

EXAMPLE 45

Polysilazane Coatings

To obtain thicker ceramic coatings, triple layered coatings of polysilazane precursors were prepared by dipping flat stainless steel plates (as in Example 44) in polysilazane/THF solutions having weight concentrations of 5% and 10%. The polysilazane used was the same as that in Example 44. Pyrolysis was conducted between each coating step according to a gradual pyrolysis regime (100° C./min temperature ramping) to a final temperature of 700° C. The coatings so prepared had a thickness of about 0.1–2.0μ and appeared substantially smooth and uniform.

EXAMPLE 46

Fiber Preparation

A polymer of type CH₃NH—(H₂SiNCH₃)$_x$—H was extended by catalytic treatment with Ru₃(CO)₁₂ substantially as discussed in Example 23. The extended polymer had an $\overline{Mn}$ of 2100 D and viscosity of 90 poise. The polymer (4.0 g) was mixed with 1.0 wt. % of monodispersed polystyrene (0.4 g) having an Mn = 1,800,000 D in 20 ml THF. The solvent was removed by evaporation after both polymers were completely dissolved in the solution. The very viscous liquid was transferred into a narrow-mouth glass container and placed under argon in a sealed glass cylinder equipped with a stainless steel wire, inlet and outlet for gases, and a heating element and thermocouple. The argon atmosphere was replaced by ammonia and fibers of 4 to 8″ were pulled out of the viscous polymer mixture by the wire. These fibers maintained their shape after a curing period of 0.5 h under ammonia without any flaws or breakage.

We claim:

1. A method of producing polysilazanes useful as preceramic polymers and containing at least one newly formed Si—N bond which comprises:
   (a) providing a precursor containing at least one Si—N bond, catalytically cleaving an Si—N bond in the precursor in the presence of a transition metal catalyst effective to activate Si—N bonds, such cleavage being carried out in the presence of hydrogen or a hydrogen donor, and reacting the cleavage product to produce an initial polysilazane product; or
   (b) providing one or more reactants which contain an Si—H bond and an N—H bond, and causing reaction to occur between such Si—H and N—H bonds in the presence of a transition metal catalyst effective to activate Si—H and N—H bonds, to produce an initial polysilazane product having at least two Si—N bonds.

2. The method of claim 1, wherein in said type (a) reaction, said initial polysilazane product results from reaction of said cleavage product is reacted with a second such cleavage product or with a compound containing an Si—H bond, an N—H bond, or both.

3. The method of claim 1, wherein a compound having an M—H bond reacts with either the cleavage product in said type (a) reaction or with a reactant in said type (b) reaction or both, wherein M is B, Al, Ga, In, Ge, Pb, Sn or S.

4. The method of claim 1, wherein the transition metal catalyst is a homogeneous catalyst selected from the group consisting of H$_4$Ru$_4$(CO)$_{12}$, Fe(CO)$_5$, Rh$_6$(CO)$_{16}$, Co$_2$(CO)$_8$, (Ph$_3$P)$_2$Rh(CO)H, H$_2$PtCl$_6$, nickel cyclooctadiene, Os$_3$(CO)$_{12}$, Ir$_4$(CO)$_{12}$, (Ph$_3$P)$_2$Ir(CO)H, NiCl$_2$, Ni(OAc)$_2$, Cp$_2$TiCl$_2$, (Ph$_3$P)$_3$RhCl, H$_2$Os$_3$(CO)$_{10}$, Pd(Ph$_3$P)$_4$, Fe$_3$(CO)$_{12}$, Ru$_3$(CO)$_{12}$, ZnCl$_2$, RuCl$_3$, NaHRu$_3$(CO)$_{11}$, PdCl$_2$, Pd(OAc)$_2$, ($\phi$CH)$_2$PdCl$_2$, and mixtures thereof, or a heterogeneous catalyst selected from the group consisting of Pt/C, Pt/BaSO$_4$, Cr, Pd/C, Co/C, Pt black, Co black, Ru black, Ra—Ni, Pd black, Ir/Al$_2$O$_3$, Pt/SiO$_2$, Ru/TiO$_2$, Rh/La$_2$O$_3$, Pd/Ag alloy, LaNi$_5$, PtO$_2$, and mixtures thereof.

5. The method of claim 1, wherein said transition metal catalyst is a palladium catalyst.

6. The method of claim 1, wherein the reaction temperature is between about $-78°$ C. and about $250°$ C.

7. The method of claim 1, wherein the polysilazanes produced are in a tractable preceramic polymer composition having either an $\overline{Mn}$ greater than about 10,000 D, an $\overline{Mw}$ greater than about 16,000 D, an $\overline{Mz}$ greater than about 40,000 D, a polysilazane species having a molecular weight higher than about 50,000 D, or combinations thereof.

8. A method of preparing silazanes and siloxazanes suitable as preceramic polymers, comprising the steps of:
   (a) providing a linear, branched or cyclic starting material having the structure —R'$_2$Si—A— in its molecule, in which A is hydrogen, NR, or Si and wherein said starting material is oligomeric, polymeric or copolymeric;
   (b) providing a transition metal catalyst effective to activate Si—N, Si—Si and/or Si—H bonds; and
   (c) reacting the starting material in the presence of such catalyst with (1) hydrogen or a hydrogen donor where A is NR and the starting material is part of a silazane or (2) H—X—R where A is hydrogen or Si, wherein:
   the R groups are independently selected from the group consisting of: hydrogen; boryl; hydrocarbyl including lower alkyl, alkenyl, alkynyl, aryl, lower alkyl substituted aryl, cycloaliphatic; silyl or polysilyl; said hydrocarbyl or silyl optionally substituted with amino, hydroxyl, an ether moiety or an ester moiety, lower alkoxy, a fused aromatic radical of 8 to 20 carbon atoms, or an organometallic radical;
   the R' moieties are independently selected from the group consisting of: hydrogen; amino; hydrocarbyl including lower alkyl, alkoxy, alkenyl, alkynyl, aryl, lower alkyl substituted aryl, cycloaliphatic; silyl or polysilyl; said hydrocarbyl or silyl optionally substituted with amino, hydroxyl, an ether moiety or an ester moiety, lower alkoxy, or a fused aromatic radical of 8 to 20 carbon atoms, and wherein R and R' may be part of an oligomeric or polymeric structure; and
   X is selected from the group consisting of NR, NR—NR, and NR—R—NR.

9. The method of claim 8, wherein the starting material is of the following structures, where x is an integer from 0 to 4 inclusive, y is an integer from 0 to 4 inclusive, z is an integer from 0 to 2 inclusive, the sum of x, y and z is 4, a and b are integers from 0 to 2 inclusive, the sum of a and b is 2, and m is an integer defining the number of monomer units in the oligomer, polymer or copolymer.

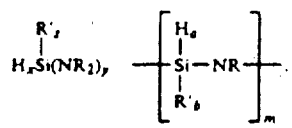

10. The method of claim 8, wherein the starting material is of the formula R'$_a$SiH$_b$ wherein a is an integer from 0 to 2 inclusive, b is an integer from 2 to 4 inclusive, and the sum of a and b is 4.

11. The method of claim 1, wherein said reaction is of type (b), said one or more reactants includes a siloxane, and said silazane products include siloxazanes.

* * * * *